(12) United States Patent
Scherer et al.

(10) Patent No.: US 10,561,586 B2
(45) Date of Patent: Feb. 18, 2020

(54) SPRAYABLE HIGH VISCOSITY COSMETIC FORMULATION

(71) Applicant: BEIERSDORF AG, Hamburg (DE)

(72) Inventors: Jonatan Scherer, Hamburg (DE); David Winterstein, Hamburg (DE); Heike Miertsch, Hamburg (DE)

(73) Assignee: BEIERSDORF AG, Hamburg (DE)

( * ) Notice: Subject to any disclaimer, the term of this patent is extended or adjusted under 35 U.S.C. 154(b) by 221 days.

(21) Appl. No.: 15/165,092

(22) Filed: May 26, 2016

(65) Prior Publication Data

US 2016/0346173 A1   Dec. 1, 2016

(30) Foreign Application Priority Data

May 28, 2015   (DE) .......................... 10 2015 209 752

(51) Int. Cl.

| | | |
|---|---|---|
| *A61K 8/04* | (2006.01) | |
| *A61K 8/31* | (2006.01) | |
| *A61K 8/92* | (2006.01) | |
| *A45D 34/04* | (2006.01) | |
| *A61K 8/34* | (2006.01) | |
| *A61K 8/35* | (2006.01) | |
| *A61K 8/43* | (2006.01) | |
| *A61K 8/49* | (2006.01) | |

(52) U.S. Cl.

CPC .............. *A61K 8/046* (2013.01); *A45D 34/04* (2013.01); *A61K 8/31* (2013.01); *A61K 8/34* (2013.01); *A61K 8/345* (2013.01); *A61K 8/35* (2013.01); *A61K 8/355* (2013.01); *A61K 8/43* (2013.01); *A61K 8/4926* (2013.01); *A61K 8/92* (2013.01); *A61K 2800/22* (2013.01); *A61K 2800/31* (2013.01); *A61K 2800/592* (2013.01); *A61K 2800/87* (2013.01)

(58) Field of Classification Search
None
See application file for complete search history.

(56) References Cited

U.S. PATENT DOCUMENTS

| | | |
|---|---|---|
| 3,770,648 A | 11/1973 | Mackles |
| 8,349,297 B2 | 1/2013 | Brown et al. |
| 8,618,081 B2 | 12/2013 | Tamarkin et al. |
| 8,663,692 B1 | 3/2014 | Mueller et al. |
| 8,795,635 B2 | 8/2014 | Tamarkin et al. |
| 2005/0106254 A1* | 5/2005 | Masaro ................... A61K 9/06 424/486 |
| 2007/0036731 A1 | 2/2007 | Hirsh et al. |
| 2008/0260655 A1* | 10/2008 | Tamarkin ............... A61K 8/046 424/45 |
| 2009/0191271 A1 | 7/2009 | Brown et al. |
| 2011/0281827 A1 | 11/2011 | Tamarkin et al. |
| 2012/0189557 A1 | 7/2012 | Hirsh et al. |
| 2013/0064777 A1 | 3/2013 | Tamarkin et al. |
| 2014/0077003 A1 | 3/2014 | Swaile et al. |
| 2014/0079649 A1 | 3/2014 | Swaile et al. |
| 2014/0248219 A1 | 9/2014 | Tamarkin et al. |
| 2015/0020915 A1* | 1/2015 | Menon .................... A61K 8/26 141/3 |
| 2016/0101184 A1 | 4/2016 | Tamarkin et al. |

FOREIGN PATENT DOCUMENTS

| | | |
|---|---|---|
| WO | 2011064631 A1 | 6/2011 |
| WO | 2014043487 A2 | 3/2014 |

* cited by examiner

*Primary Examiner* — Brian Gulledge
(74) *Attorney, Agent, or Firm* — Abel Schillinger, LLP

(57) ABSTRACT

The invention relates to an anhydrous cosmetic or dermatological formulation comprising a viscose lipid-containing preparation and propellant gas consisting essentially of one or more substances selected from hydrofluorocarbons, n-butane, isobutane and propane. The formulation permits application to the skin by spraying of an otherwise nonsprayable preparation. The formulation is free from readily volatile solvents, surfactants, and preferably free from silicones.

1 Claim, 10 Drawing Sheets

Streaks

Filling

Streaks

Filling

Streaks

Filling

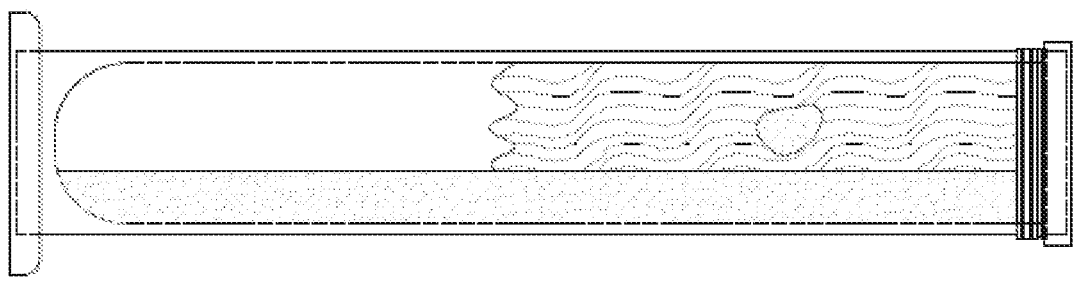
Figure 4
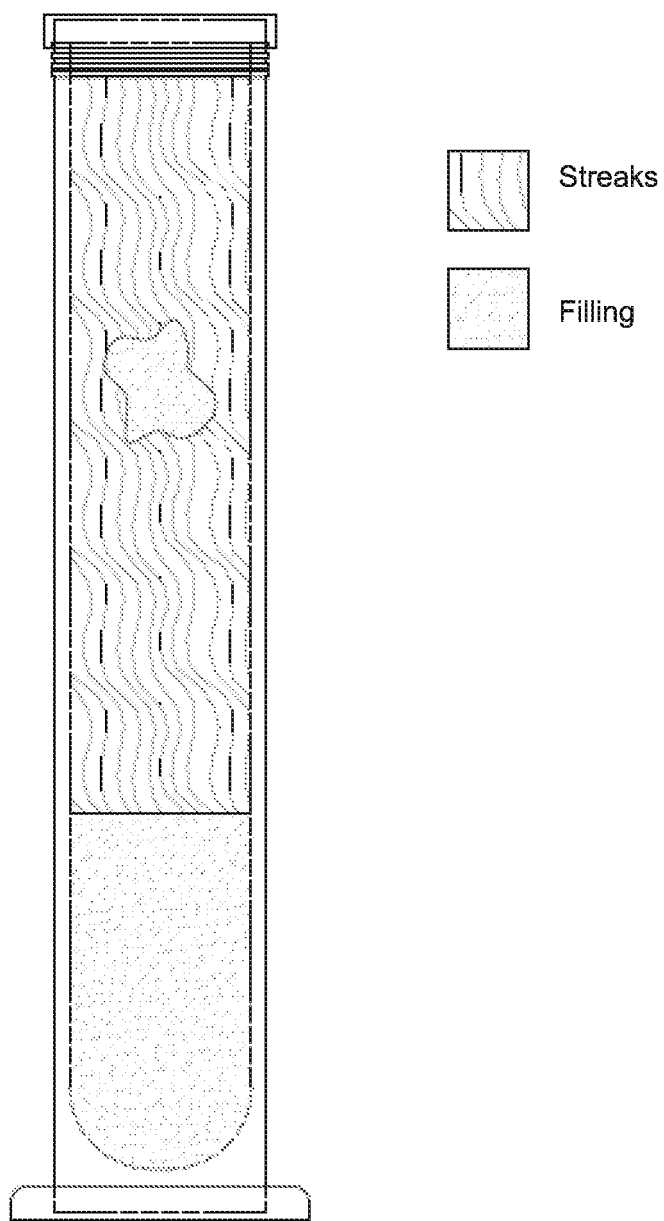

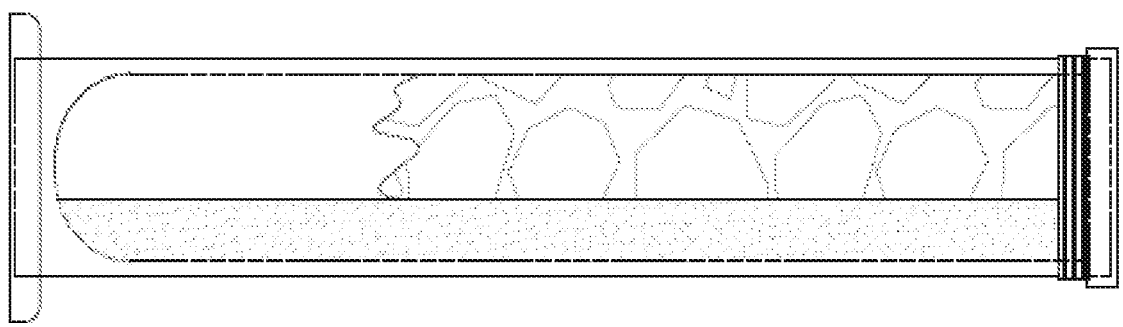
Figure 6
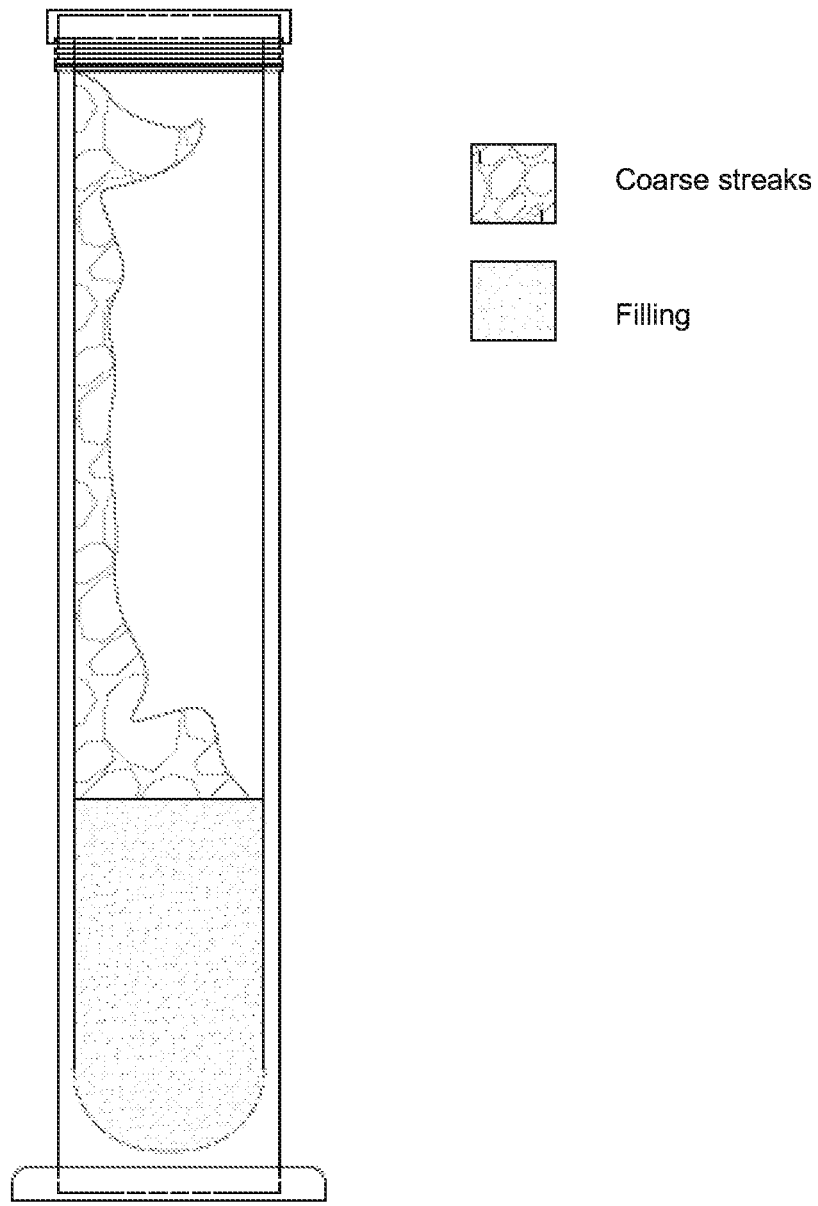

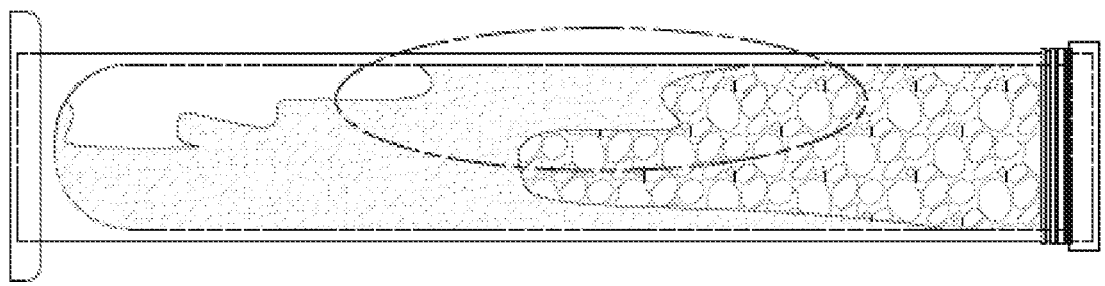
Figure 9
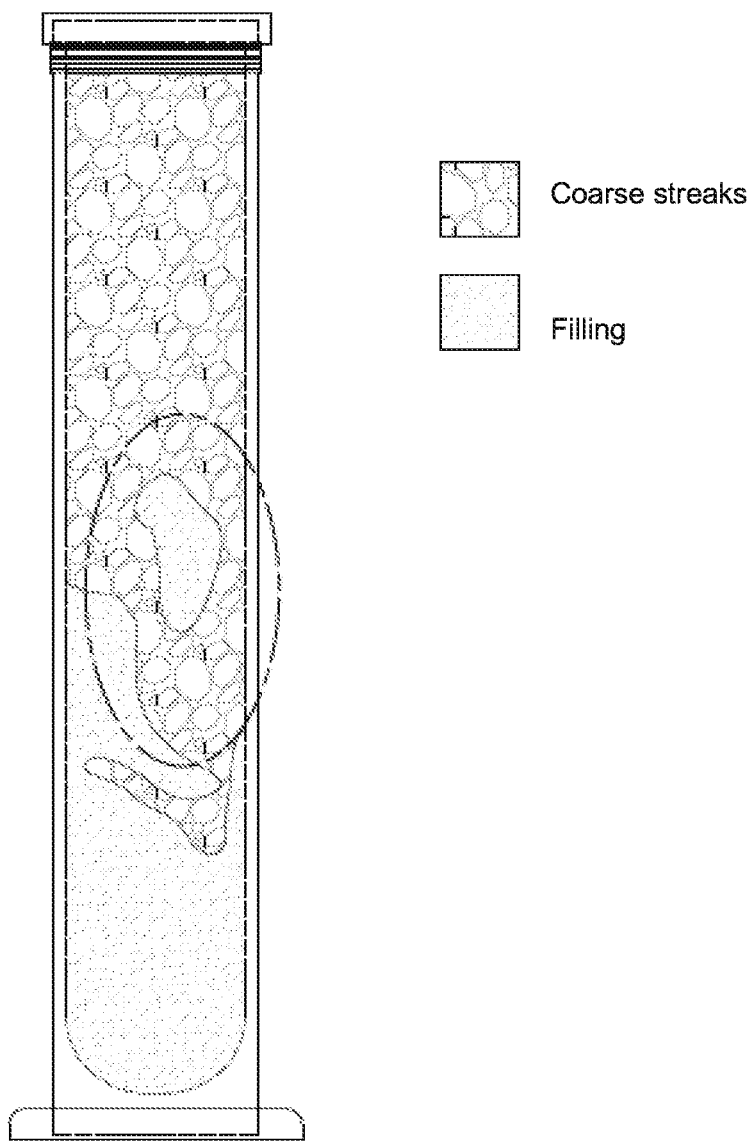
Coarse streaks
Filling

SPRAYABLE HIGH VISCOSITY COSMETIC FORMULATION

CROSS-REFERENCE TO RELATED APPLICATIONS

The present application claims priority under 35 U.S.C. § 119 of German Patent Application No. 102015209752, filed May 28, 2015, the entire disclosure of which is expressly incorporated by reference herein.

BACKGROUND OF THE INVENTION

1. Field of the Invention

The present invention relates to a sprayable cosmetic or dermatological formulation comprising a lipid-containing preparation and one or more propellant gases selected from hydrofluorocarbons, n-butane, isobutane and propane.

The formulation permits the application of a cosmetic preparation to the skin by spraying an otherwise non-sprayable preparation.

2. Discussion of Background Information

In known aerosol atomizers or spray cans, a liquid contained therein is held under pressure by a propellant present in the container and is expelled through a nozzle to form an atomized jet. Constituents of the spray can are the liquid and/or gaseous propellant since this generates the necessary pressure for spraying, and the actual product—the active ingredient, the preparation, which is to be sprayed. The product to be applied is gaseous or liquid and/or mixed in the can with the propellant, the propellant gas.

As a result of the internal pressure in the spray can, its contents are released precisely as aerosol if the spray head is pressed. The secret of this function mode lies in the mixture of active ingredient (the actual product) and liquid propellant inside of the spray can: some of the propellant is dissolved in the active ingredient and some is in gaseous form as "pressure cushion" above the active ingredient/propellant mixture. If the spray head is actuated, the gaseous propellant forces the contents through the valve to the outside. At this moment, the propellant evaporates in fractions of seconds and the remaining active ingredient distributes itself finely and evenly.

Some active ingredients cannot be mixed directly inside the can with a propellant. For example, the active ingredients/products/preparations to be discharged are often unstable towards the propellant.

In particular, products which are per se sprayable only with difficulty, if at all, such as high viscosity formulations, such as pastes, creams or high viscosity gels or emulsions, can be sprayed with difficulty or not at all.

With the help of aerosol technology and the packaging format of the "two-chamber aerosols", these cream-like or thick-liquid substances can be contained in a spray can and discharged from this. However, in the so-called "bag-in-can" or "bag-on-valve" systems, the propellant gases are not in direct contact with the formulations to be discharged.

In further known cosmetic aerosol preparations, the propellant gases are predominantly mixtures of butane, isobutane and propane at a pressure level of 2.7 bar.

Frequent presentation forms of these cosmetic or dermatological preparations are finely dispersed multiphase systems in which one or more fat or oil phases is/are present alongside one or more water phases. Among these systems, the actual emulsions are in turn the most widespread.

The term "cosmetics" summarizes all measures which, for esthetic reasons, bring about changes to skin and hair or are used for cleaning the body. Cosmetics thus means to care for, to improve and/or to beautify the outside of the body in order to please, in a visible, palpable and olfactory manner, both fellow beings as well as oneself. Cosmetics has been used by people for this purpose for centuries. This included coloring lips and face, anointing with valuable oils and bathing in scented water.

One property of cosmetic products that is very important to the consumer but can only be quantitatively measured with difficulty is their texture. The term "texture" is understood as meaning those properties of a cosmetic which are attributed to the structure of the preparation, are perceived by the sense of touch and contact and can possibly be expressed in mechanical or rheological flow properties. The texture can be tested in particular by means of sensorics. The texture of cosmetic products that may be influenced with the help of additives is of virtually identical importance to the consumer as their objectively ascertainable effects.

The term "sensorics" is used to refer to the scientific discipline which deals with the evaluation of cosmetic preparations on the basis of sensory impressions. The sensory assessment of a cosmetic takes place by reference to the visual, olfactory and haptic impressions.

Visual impressions: all features perceptible to the eye (color, shape, structure).

Olfactory impressions: all odor impressions perceptible upon drawing in air through the nose, which can often be differentiated into initial odor (top note), main odor (middle note, body) and end note (finale). The volatile substances released only upon application also contribute to the olfactory impression.

Haptic impressions: all sensations of the sense of touch, which relate primarily to structure and consistency of the product.

The sensory analysis makes use of the possibility of integrally ascertaining the sensory overall impression of a product. Disadvantages of sensory analysis are the subjectivity of the impression, the easy influencing of the subjects and the considerable scattering of the results brought about as a consequence. These weaknesses are countered nowadays by using groups of trained subjects, mutual screening of the examiners, as well as statistical evaluation of the mostly numerical analysis data.

The removal, application and spreading of high viscosity preparations on the skin is furthermore beset with problems for the user and is often unacceptable from a sensory perspective.

The very removal and application of thick-liquid or pasty preparation using the fingers from a jar or a tube is unpleasant or difficult to dose. It would be desirable to provide a contactless removal option.

Contactless application means, for example, by means of a spatula or spoon or by being able to spray the preparation.

However, high viscosity substances are not easy to spray without considerable expenditure in terms of apparatus or formulation technology.

It was therefore an object to provide topical formulations comprising lipid-containing, in particular high viscosity, preparations which can be applied in a contactless manner and can be applied to and spread on the skin in an easy and sensorily acceptable manner.

Preferred topical preparations are cosmetic, dermatological or pharmaceutical preparations, in particular cosmetic preparations.

Moreover, it is desirable to provide an application option for different cosmetic or dermatological preparations.

Cosmetic aerosols, such as e.g. deodorants, are known. However, these usually comprise emulsions and are water-containing.

Moreover, foot sprays are known, such as the spray from Aurena® as Petrolatum Spray or Apresan® and Scholl® foot spray. The latter are again water-containing preparations, emulsions which moreover comprise a customary propellant gas mixture.

The petrolatum foot spray is a so-called bag-on-valve system, meaning that there is no direct contact between the propellant gases and the preparation to be applied contrary to the desired execution.

U.S. Pat. No. 8,795,635 B2, the entire disclosure of which is incorporated by reference herein, describes foamable preparations comprising, besides customary propellant gases, 25 to 95% of petrolatum, 1 to 70% of a hydrophobic solvent and 0.1 to 20% of an agent which is responsible for the foam formation, in particular surfactants. The preparations are free from water, short-chain alcohols and silicones.

US 20120189557 A1, the entire disclosure of which is incorporated by reference herein, discloses formulations containing propellant gas which, for the application of cosmetic or pharmaceutical preparations, require the addition of readily volatile carrier liquids, in particular readily volatile silicones.

WO 20140434487 A2, the entire disclosure of which is incorporated by reference herein, describes antiperspirant preparations which have a propellant gas fraction of 30 to 65% by weight. The viscosity of the propellant-gas-free preparation is more than 1000 cP. In order to be able to apply these preparations as aerosol, a fraction of nonvolatile silicones of more than 40% by weight is prescribed as being obligatorily necessary.

WO 2011064631 A1 and US 20130064777 A1, the entire disclosures of which are incorporated by reference herein, describe water- and surfactant-free preparations which comprise hydrophobic solvents, a wax and propellant gases. The propellant gas fraction here is at most 30% and preferred propellant gases are mixtures of propane, isobutane and butane with at most 27% n-butane. For propellant gas fractions above 30%, no foams are obtained according to the description.

U.S. Pat. No. 8,663,692 B1, the entire disclosure of which is incorporated by reference herein, describes lipid particle dispersions of a mixed matrix of solid lipid and liquid lipid. The dispersions can be sprayed, possibly following dilution with water, using standard commercial devices or be atomized as aerosol. An essential constituent here is water or a water-miscible liquid.

U.S. Pat. No. 8,349,297 B1, the entire disclosure of which is incorporated by reference herein, describes a pharmaceutical formulation which, upon topical administration, can form a film, where the formulation has a preparation of a pharmaceutical, a solvent therefor, a film former and a propellant.

So-called Vaseline sprays are known from another technology sector, the building sector.

These include solvents such as petroleum spirit or alcohols which are able to dissolve the Vaseline so as then to allow discharge using known propellant gases and apparatuses.

Alcohols, in particular short-chain alcohols, such as ethanol or isopropanol, can dry out the skin and often lead to burning, unpleasant cooling effect and/or skin irritations upon application.

It would therefore be advantageous to have available a topical, preferably cosmetic, formulation which does not have the disadvantages of the prior art. A problem here is that avoiding one disadvantage often leads to another disadvantage.

It is therefore desirable to provide a formulation where the number of ingredients can be limited to a minimum. In particular, it is necessary to dispense with skin-irritating, readily volatile substances, such as solvents, e.g. ethanol or petroleum spirit, foam formers, such as surfactants, and with silicones since these would hinder the skincare aspect and in particular the application-friendly application.

SUMMARY OF THE INVENTION

The present invention provides a topical, in particular cosmetic, pharmaceutical and/or dermatological formulation comprising a lipid-containing preparation which preferably has a consistency of from 50 to 70 units at 25° C. measured using a consistometer such as, e.g. a KO-82 consistometer. The lipid-containing preparation is in direct contact with a propellant gas. The propellant gas consists essentially of one or more substances selected from hydrofluorocarbons (HFC) and the hydrocarbons n-butane, isobutane and propane.

"Essentially" means that small amounts (e.g., less than 2%, less than 1%, less than 0.5%, less than 0.1% or less than 0.05% based on the total mass of the propellant gases) of other propellant gases may be present due to impurities or entrainments, without adversely affecting the inventive effects. Ideally, the propellant gas consists of one or more substances selected from hydrofluorocarbons, n-butane, isobutane and propane.

Preferably, the propellant gas consists of n-butane, either alone or in combination with isobutane and/or propane. Advantageously, the weight ratio of n-butane to the other propellant gases is in the range from 100% by weight:0% by weight to 90% by weight:10% by weight, based on the total mass of the propellant gases. The variant with 100% means that only n-butane is present as propellant gas. In the other cases, a preferred ratio of n-butane to the other propellant gases is in the range from 99.9% by weight:0.1% by weight to 90% by weight:10% by weight, based on the total mass of the propellant gases.

As an essential difference compared to the prior art, additional solvents which permit dissolution and thus spraying of the high viscosity lipid-containing preparation according to the prior art are dispensed with. The fraction of ethanol, isopropanol, methanol and petroleum spirit is therefore in each case less than 0.1% by weight, e.g., less than 0.05% by weight, in particular less than 0.01% by weight, e.g., 0% by weight, based on the total mass of the formulation.

The formulation is ideally anhydrous. However, since water can enter on account of impurities, entrainments due to the production process or during storage, the fraction of water in the formulation is less than 2% by weight, e.g., less than 1% by weight, or less than 0.5% by weight, and in particular less than 0.1% by weight, based on the total mass of the formulation, in order to still qualify as "anhydrous".

Ideally, the formulation is free from solvents with a boiling point in the range from 30° C. to 150° C.

The addition of surfactants and particularly preferably all foam formers is likewise dispensed with.

Furthermore, the lipid-containing preparation is in direct contact with the propellant gas, meaning that bag-in-can or bag-on-valve systems can likewise be dispensed with.

A further feature according to the invention is that the weight fraction of the lipid-containing preparation relative to the propellant gas is less than 70% by weight, e.g., less than 69.5% by weight, less than 69% by weight, or less than 68% by weight, based on the total mass of the formulation consisting of preparation and propellant gas.

Preferably, the weight ratio of lipid-containing preparation to the propellant gas should be selected in the range from 69% by weight:31% by weight to 10% by weight:90% by weight, in particular from 65% by weight:35% by weight to 10% by weight:90% by weight, in particular in the range from 60% by weight 40% by weight to 40% by weight:60% by weight, in particular in the range from 55% by weight: 45% by weight to 45% by weight:55% by weight, very particularly preferably in the range from 51% by weight: 49% by weight to 49% by weight:51% by weight, e.g., close to or equal to 50% by weight:50% by weight, based on the total mass of the formulation.

Preferably, the weight ratio of preparation to the propellant gas is in the range from 60:40 to 40:60, e.g., 50:50. In other words, ratios preferred according to the invention are:

| % by weight lipophilic preparation | % by weight propellant gas |
|---|---|
| 61 | 39 |
| 60 | 40 |
| 59 | 41 |
| 58 | 42 |
| 57 | 43 |
| 56 | 44 |
| 55 | 45 |
| 54 | 46 |
| 53 | 47 |
| 52 | 48 |
| 51 | 49 |
| 50 | 50 |
| 49 | 51 |
| 48 | 52 |
| 47 | 53 |
| 46 | 54 |
| 45 | 55 |
| 44 | 56 |
| 43 | 57 |
| 42 | 58 |
| 41 | 59 |
| 40 | 60 |
| 39 | 61 |

Preferred selections regarding the propellant gas are only n-butane and propane, only isobutane and n-butane, only isobutane or only propane, preferably only n-butane or only isobutane, in particular only n-butane.

The formulations preferred according to the invention comprise high viscosity lipid-containing preparations.

High viscosity liquids, such as honey or syrup, have dynamic viscosities at 25° C. of more than 10 000 mPa*s.

Preferably, the lipid-containing preparation according to the invention has a dynamic viscosity of more than 10 000 mPa*s, determined at 25° C. and a shear rate of 10 s$^{-1}$. In particular, the lipid-containing preparation may have a dynamic viscosity in the range from 15 000 to 30 000 mPa*s, in particular in the range from 18 000 to 25 000 mPa*s at 25° C. and a shear rate of 10 s$^{-1}$.

The preparation preferably has a markedly high consistency of from 50 to 70 units. The consistency is measured using a consistometer, e.g. the KO-82 consistometer, at 25° C.

At this viscosity or consistency, a sprayability of the preparation is difficult or not possible at all without high expenditure on apparatus and without the addition of solvents, as proposed in the prior art.

Viscosity is the term used to refer to the measure of internal friction of liquid substances, a measure of the ropiness of a fluid. The inverse parameter of viscosity is the fluidity, a measure of the flowability of a fluid. The greater (or higher) the viscosity, the thicker, i.e. less flowable, the fluid; the lower the viscosity, the more thin-liquid it is, and the higher the fluidity.

A distinction is made between dynamic and kinematic viscosity. The dynamic viscosity is given in Pa·s (Pascal second) and is determined in most cases with the help of a rotary viscometer. The kinematic viscosity is measured in m$^2$/s. It indicates the internal friction of a liquid and is calculated by dividing the dynamic viscosity by the density of a liquid.

The consistency is in turn the resistance of a substance to its deformation.

A known instrument for investigating the flow properties of high viscosity substances is the Höppler consistometer.

The lipid-containing preparation is a high viscosity preparation and, according to the invention, preferably has a consistency of 50 to 70 units, measured using a consistometer at 25° C.

The measuring device of a consistometer such as the KO-82 consists of a conventional leaf spring with lateral deflection. On a dynamometer, its sensor is equipped with an 8 mm polyamide ball. By means of a joining device, there is a link to a DC driven motor which has a speed around the rotational axis of 10 rpm.

The test vessels to be used are aluminum cans in sizes 60 ml (standard size), 150 ml or 250 ml.

The consistency measurement is carried out 20 to 24 hours after the preparation or filling of the cream in aluminum cans. The temperature of the cream is fixed at 25° C. (deviation of +/−0.2° C. (DIN 53019)). On the drive axis, a scale with 10-100 scale divisions is chosen.

The measurement of the dynamic viscosity can be carried out for example with the following instruments and/or parameters:

Instrument: ARES 6
Measurement: FREQ (frequency test)
Measurement temperature: 25° C.
Measurement system: plate/plate 50 mm, 1 mm gap
Program: 0.1 rad/s to 100.0 rad/s According to the invention, it is possible only through the specifically selected propellant gas, the stipulated weight ratios of preparation and propellant gas and the dispensing with certain constituents, to discharge a high viscosity preparation by means of an aerosol device.

Accordingly, the use of propellant gas consisting essentially of one or more substances selected from the group hydrofluorocarbons, n-butane, isobutane and propane for discharging an anhydrous, high-viscosity lipid-containing preparation from an aerosol vessel, wherein the propellant gas is in direct contact with the preparation and the weight fraction of the lipid-containing preparation is less than 70% by weight, based on the total mass of the preparation and propellant gas, is also in accordance with the invention.

In the formulation according to the invention, the propellant gas is in direct contact with the preparation to be discharged, i.e. two-chamber containers are not necessary.

According to the invention, to better define the terminology and for the purposes of differentiation, the term "preparation" is used to describe the propellant-gas-free composition and the term "formulation" is used to describe the propellant-gas-containing composition.

According to the invention, topical applies to all those formulations, preparations, compositions which can be applied to the human body (skin) and in particular, do not contain any components which would be harmful to the human body and in particular, human skin.

The sprays known in the prior art from the building sector are not included here.

The lipid-containing preparation is advantageously formulated as ointment. According to the invention, ointment (latin Unguentum) or cream is understood as meaning a semisolid preparation that advantageously appears homogeneous and which is intended for use on the skin (e.g. as wound ointment) or on the mucosa. Ointments serve for the local application of active ingredient or for the care and protection of the skin, wounds or mucosa.

It consists primarily of a greasy base of natural or synthetic substances and can be a single-phase (e.g. Cera Microcristallina or Paraffinum liquidum) or multiphase system. Active ingredients or medicaments can be incorporated in solution or dispersion in the ointment or cream. The release of active ingredients from the ointment is possible and preferred according to the invention.

In the context according to the invention, the term ointment includes
  ointments in the strict sense, single-phase,
  creams,
  gels, lotions and
  pastes The ointment used, which is particularly preferably anhydrous, is in particular petrolatum or mixtures comprising petrolatum. Besides or instead of petrolatum, the ointment can preferably also comprise mineral oil, ceresin and/or lanolin alcohol.

Active ingredients may be present in the ointment or cream. Active ingredients are in particular natural additives.

The lipid-containing preparation used may preferably be an ointment, such as a commercially available ointment, such as, for example, Aquaphor® (with or without dexpanthenol) or Vaseline®.

Likewise, the use of at least one active ingredient selected from the anti-inflammatory or wound-healing-promoting active ingredients for local pain alleviation and inflammation inhibition is a particularly preferred application.

Moreover, the use of at least one active ingredient selected from antiseptics, antibiotics and antimycotics has proven advantageous for local wound disinfection and/or reducing germ colonization.

Advantageously, the preparation may comprise anti-inflammatory, wound-healing-stimulating, pain-alleviating or antimicrobial active ingredients.

For example, the preparation may comprise anti-inflammatory or wound-healing-promoting active ingredients such as zinc acetate $2H_2O$, zinc sulfate $7H_2O$, allantoin, Aloe Vera, arnica, bisabolol, calendula, chamomile, dexpanthenol, enzyme inhibitors, hamamelis, urea, honey/Manuka honey, hyaluronic acid, St. John's Wort, chamomile extract, polidocanol, propolis, vitamins or provitamins, growth factors, e.g. PDGF, wheatgerm extract, zinc oxide, vitamin A, vitamin C, vitamin E, chitosan, Capsicum annuum L. and derivatives, benzydamine, benzyl nicotinate, bufexamac, diclofenac, etofenamate, flufenamic acid, heparinoids. Ibuprofen, indometacin, ketoprofen, naxoprophen, piroxicam, salicylic acid and its derivatives, teniposide, 2-hydroxybenzoic acid, acetylsalicylic acid and derivatives. Acid. silicicum D8, Aconitum (Wolf's bane), Aconitum D3, Aescin (horse chestnut), D4 ("cow parsley"), ammonium bituminosulfonate (ICHTHYOL®), Arnica D3, Arnica mont. D4, Arnica montana ex herba rec. ad usum ext, extract from guaiac wood, extract from Arnica montana, Balsamum peruvianum (Peru balsam), comfrey root fluid extract, benzyl nicotinate, Calendula ad usum ext, Calendula D3, CalendulaØ, Calendula offic. D3, Calendula officinalisØ, camphor, chamomile, Colchicum e seminibus D4, Conium D2, Cork. Heisteriae, Cort. Salicis, D-camphor, delphinium staph (larkspur), Delphinium staph. D4, dexpanthenol, diclofenac-diethylamine, diclofenac-sodium, diethylazane salt, dimethyl sulfoxide, Echinacea ang., EchinaceaØ, Echinacea purp., Echinacea purp. Ø, Echinacea purpurea, Planta totaØ, true goldenrod, etofenamate, Extr, Flor Calendulae spiss, Extr. Fol Digitalis fluid, Extr. Fol Hyoscyami fluid, Extr. Herba Conii maculate, Extr. Rad. Petasit. Spiss, Extr. Rhiz. Podophylli fluid., Extr. Semen Colchici fluid, Ferrum phosphoricum D10, spruce needle oil, flufenamic acid, Fol. Betulae, GuaiacumØ (guaiac resin), guaiac wood dry extract, Hamamelis D4 ("witchhazel"), Harpagophytum procumbens, Helianthus ann. D4, Hepar sulf. D8, Hepar sulfuris, heparin-sodium, humic acids, hydroxyethyl salicylate, hypericum, Ibuprofen, indometacin, isobornyl acetate, Potassium bichrom. D8, Potassium sulf. D8, potassium-iron-phosphate-citrate complex, ketoprofen, Lachesis mutus D8, dwarf pine oil, Levisticum, Rad. sicc. H 10%, levomenthol, Mercurialis perennis 2bØ, Mercurius bijodatus D5, Mercurius solub. Hahnem, Mercurius solub. Hahnem. D8, methyl nicotinate, methyl salicylate (salicylic acid methyl ester), millefolium, myrtecain, naloxon HCl, sodium thiosulfate, natural eifelfango, nicoboxil, paracetamol, Pl. tota rec, quartz, Rad. Harpagophyti (Devil's claw), Rad. Harpagophytum procumbens, Resina Laricis (Terebinthina laricina), Rhus toxicodendron D6, Ruta D6 (rue), salicylic acid, sulfur, Stibium metallicum praeparatum, Stibium sulfuratum nigrum D1, Symphytum (comfrey), Symphytum D6, Symphytum offic. e rad. D6, Devil's claw root extract, tilidine-HCl $0.5H_2O$, tilidine phosphate, toxin of Vipera ammodytes, tramadol-HCl, extract from stinging nettle leaves, extract from horse chestnut seeds, extract from willow bark, extracts of aspen bark and leaves and/or triclosan.

Particularly preferably, one or more of dexpanthenol, allantoin, bisabolol, urea, honey, e.g. Manuka honey, hyaluronic acid, licochalcone, in particular licochalcone-A, polidocanol, propolis, zinc oxide, vitamins and/or provitamins such as e.g. Vitamin A, C or E, may be present in the preparation.

Derivatives and related and similar substances, also in combination or in combination with other substances, may also be present. Aloe Vera, calendula, chamomile, hamamelis, St. John's Wort, wheatgerm, eucalyptus and extracts thereof or active ingredient combinations with these substances can also be present. Further possible wound-healing-promoting active ingredients are other wound-healing-promoting plant substances or substance mixtures or plant extracts. The use of one or a combination of the listed substances promotes wet wound healing.

Very particular preference is given to one or more of dexpanthenol, bisabolol, licochalcone A, polidocanol. These substances can advantageously be used in the preparation in a concentration of, e.g., from 0.05 to 5% by weight, preferably in a concentration of from 0.1 to 3% by weight, in particular from 0.5 to 2.5% by weight, based on the total mass of the preparation.

Zinc oxide is likewise particularly preferred and may be used in the preparation in a concentration of, e.g., from 0.05 to 20% by weight, preferably in a fraction of from 0.1 to 10% by weight, in particular from 0.5 to 5% by weight, based on the total mass of the preparation.

Further possible active ingredients present in the preparation include local anesthetics which are suitable for surface anesthesia, such as e.g. Arsenicum album D12 (white arsenic), articaine, articaine HCl with epinephrin HCl, atropium sulf. D5, benzalkonium chloride, benzocaine, bupivacaine, bupiviacine-HCl, chloroethane, cinchocaine, dibucaine, etidocaine, fomocaine, Formica rufa D12 (red wood ant), Hypericum perf. D5, lidocaine, lidocaine-HCl, mepivacaine, mepivacaine-HCl, methyl 4-hydroxybenzoate, oxybuprocaine, oxybuprocaine-HCl, prilocaine, procaine, procaine-HCl, procaine-HCl with caffeine, propyl 4-hydroxybenzoate, quinisocaine, ropivacaine, ropivacaine-HCl, sulfur D12, tetracaine, tetracaine-HCl with macrogol lauryl ether and/or liquorice extracts.

Active ingredients for local pain alleviation such as, for example, benzocaine, procaine, lidocaine or prilocaine may be very particularly advantageously present in the preparation.

The use of local anesthetics offers the additional benefit of rapid pain alleviation of an injured skin site. Local anesthetics may be used in the preparation in a concentration of, e.g., from 0.01 to 4% by weight, preferably in a concentration of from 0.05 to 3% by weight, in particular from 0.5 to 2.5% by weight, based on the total mass of the preparation.

Further particularly advantageous active ingredients include cyclooxygenase inhibitors for pain alleviation and inflammation inhibition, such as, for example, acetylsalicylic acid or nonsteroidal antirheumatic (NSAIDs) such as, for example, diclofenac, ibuprofen, ketoprofen, benzydamine, benzyl nicotinate, bufexamac, etofenamate, flufenamic acid, heparinoids, naxoprophen, piroxicam, teniposide or indometacine. Derivatives thereof as well as related and similar substances, also in combination or in combination with other substances, may be present in the preparation in order to offer an additional pain-alleviating effect. Cyclooxygenase inhibitors may be present in a concentration of, e.g., from 0.01 to 10% by weight, preferably in a fraction of from 0.1 to 5% by weight and particularly preferably in a concentration of from 0.2 to 2.5%. Plant pain-alleviating agents such as, for example, aescin, guaiac wood, Rhiz. Podophylli, Herba Conii, Fol Hyoscyami, Fol Digitalis, Echinacea purpurea, ash bark, Delphinium staph, camphor, balsamum peruvianum, comfrey root, goldenrod and aethusa, as well as extracts and combinations thereof can also very advantageously be present in the preparation, advantageously in a concentration of, e.g., from 0.1 to 5% by weight, particularly advantageously in a concentration of from 0.5 to 3% by weight, based on the total mass of the preparation.

The preparation may also comprise antiseptic, antibiotic or antifungicidal active ingredients. An antiseptic effect prevents infections of the wound and thereby offers an additional benefit of the formulation according to the invention.

Antiseptic, antibiotic and antifungicidal/antimycotic active ingredients, which include inter alia the aminoglycosides, prevent infections by preventing the growth of microorganisms. The following are to be mentioned as being advantageous and advantageously present: antimicrobial metals, for example silver, elemental or salts thereof, chlorhexidine, octenidine hydrochloride, polyhexanide, povidone-iodine, taurolidine, 2,2'-methylenebis(6-bromo-4-chlorophenol), 2-biphenylol, 3,5-dibromo-4-hydroxybenzenesulfonic acid, 5-chloro-2-hydroxybenzoic acid, aluminum acetate tartrate, benzalkonium chloride, benzyl alcohol, biphenyl-2-ol, clorofen, butane-1,3-diol, quinolin-8-ol sulfate, quinolinol sulfate potassium sulfate, chlorhexidine bis (D-gluconate), chlorhexidine digluconate, coconut propylenediamine, didecyldimethylammonium chloride, ethacridine lactate 1H$_2$O, glucoprotamine, glutaral, potassium thiocyanate, mecetronium etilsulfate, methyl 4-hydroxybenzoate, octenidine-2HCl, phenoxyethanol, polyhexanide, povidone-iodine, propyl 4-hydroxybenzoate, tosylchloramide-sodium 3H$_2$O, undecylenic acid, hydrogen peroxide, bifonazol, ammonium bituminosulfonate, bacitracin, benzoyl peroxide, quinolin-8-ol sulfate, chloramphenicol, chlorotetracycline-HCl, clindamycin, clindamycin 2-dihydrogenphosphate, clioquinol, erythromycin, framycetin sulfate (neomycin B), fusidic acid 0.5H$_2$O, gentamycin sulfate, purified turpentine oil, imiquimod, isotretinoin, larch terpentine, meclocyclin (5-sulfo-2-hydroxybenzoate), metronidazole, miconazole nitrate, mupirocin, nadifloxacin, sodium bituminosulfonate (ICHTHYOL®-sodium), sodium fusidate, neomycin sulfate, oxytetracyclin-HCl, podophyllotoxin, retapamulin, sulfadiazine-silver, tetracycline-HCl, tretinoin, dry extract from Melissa leaves, tyrothricin. Particularly advantageously, chitosan, chlorhexidine, povidone-iodine, silver or sulfadizine-silver, triclosan, octenidine hydrochloride, polyhexanide, taurolidine or fungicides may be present.

Derivatives, similar substances and combinations thereof are thus also encompassed according to the invention. Plant antiseptic substances such as purified turpentine oil or larch turpentine can likewise be present as active ingredients in the preparation.

In the case of the antiseptic active ingredients, particular preference is given to silver and its salts, octinidine and its derivatives, in particular octinidine dihydrochloride (octinidine and its derivatives also in combination with phenoxyethanol), iodine and its derivatives, povidone-iodine, polyhexanide and its derivatives, in particular polyhexanide hydrochloride, chlorhexidine and its derivatives, in particular chloride and acetate, here in particular chlorhexidine digluconate.

Antiseptic active ingredients may be present in the preparation in a concentration of, e.g., from 0.1 to 10% by weight, preferably in a concentration of 0.5 to 3% by weight, preferably in a concentration of 0.5 to 5% by weight, based on the total mass of the preparation. Further antiseptic active ingredients such as e.g. ethacridine lactate, may be present in a concentration of, e.g., from 0.05 to 1% by weight, advantageously in a fraction from 0.1 to 0.5% by weight.

In the case of the antimycotic active ingredients, particular preference is given to the selection of ketoconazole, micronazole, ciclopirox (or its ethanolamine salt ciclopirox olamine), amorolfine and its derivatives, naftifine, pyrrolnitrin, terbinafine, bifonazole and/or clotrimazole.

Antimycotic active ingredients may be present in the preparation in a concentration of, e.g., from 0.1 to 10% by weight, preferably in a concentration of 0.5 to 3% by weight, preferably in a concentration from 0.5 to 5% by weight, based on the total mass of the preparation.

Active ingredients for the more rapid healing of herpes blisters may be particularly preferably present in the preparation. Examples include heparin-sodium, foscarnet-sodium, tromantadine, idoxuridine, dimethyl sulfoxide, pencicolvir and aciclovir. Besides the wet wound healing, a virustatic active ingredient offers an additional effect for a more rapid healing of herpes blister outbreaks. Virustatics may advantageously be present in a concentration of, e.g., from 1 to 10% by weight, preferably in a concentration of from 3 to 8% by weight. Plant virustatics such as e.g. extracts from Melissa leaves may be present in a concentration of, e.g., from 1 to 20% by weight, advantageously in a concentration of from 5 to 15% by weight. Unless stated otherwise, the concentration data refer to the total mass of the preparation.

It is preferred that cosmetic, in particular skincare active ingredients are present in the preparation.

Active ingredients selected from glycerin, panthenol, bisabolol, gylcyrrhetic acid, urea, arctin, alpha-lipoic acid, folic acid, phytoene. D-biotin, coenzyme Q10, alpha-glucosylrutin, tocopheryl acetate, carnitine, carnosine, caffeine, natural and/or synthetic isoflavonoids, glycerylglucose, creatin, creatinine, taurine, magnolia, β-alanine and/or licochalcone A may advantageously be present.

If present, the active ingredient or ingredients are present advantageously in a concentration of 0.001-10% by weight, preferably 0.01-5% by weight, particularly preferably 0.05-1% by weight, preferably 0.01-0.5% by weight, based on the total mass of the preparation.

A preferred formulation according to the invention comprises a lipid-containing preparation with a particularly high viscosity or consistency, and propellant gas consisting advantageously only of n-butane, where the lipid-containing preparation is in direct contact with the propellant gas and the weight fraction of the lipid-containing preparation relative to the propellant gas is in the range from 45:55 to 55:45, based on the total mass of the formulation consisting of lipid-containing preparation and propellant gas.

In this specific embodiment, preference is given to dispensing with the addition of readily volatile solvents with a boiling range from 30° C. to 150° C. Preference is also given to dispensing with the addition of silicones and surfactants.

The preparations according to the invention are advantageously anhydrous, preferably free from short-chain alcohols with two to six carbon atoms and ideally comprise no further solvent with a boiling point of from 30° C. to 150° C.

The preparation according to the invention is likewise advantageously free from surfactants, in particular free from foam formers.

Furthermore, the fraction of silicones, provided not already excluded on account of the boiling ranges, may be less than 40% by weight, e.g., less than 20% by weight, or less than 10% by weight, in particular less than 5% by weight, less than 2% by weight, or less than 1% by weight, based on the total mass of the preparation (without propellant gases). The preparation is preferably free from silicones.

"Free from" means that traces of these substances may be present in the preparations, for example entrained in the preparation process or due to impurities in the raw materials used. A fraction of less than 0.1% by weight, preferably less than 0.05% by weight, less than 0.02% by weight, or less than 0.01% by weight of one or more of these substances, based on the total mass of the preparation without propellant gases, always still means free from these substances according to the invention.

For water, the maximum upper limit is 2% by weight in order to qualify as anhydrous so that any entrainments, which have no influence at all on the formulation properties, are included. Preferably, the preparation will contain less than 500 ppm, e.g., less than 400 ppm, less than 300 ppm, or less than 250 ppm of (entrained) water.

In other words, the preparation according to the invention, which may comprise, for example, 0.01% by weight of water and/or 0.005% by weight of surfactants, nevertheless still qualifies as being anhydrous and/or free from surfactants. In these traces, the corresponding effects of these substances, for which reason the person skilled in the art adds them deliberately in a higher amount, e.g. foam formation as a result of surfactants or dissolution properties of alcohols are not present. A "free from" in accordance with the invention is thus given for the person skilled in the art.

Surfactants are substances which reduce the surface tension of a liquid or the interfacial tension between two phases and permit or assist the formation of dispersions. Surfactants have the effect that two liquids that are actually immiscible with one another, such as for example oil and water, can be dispersed.

Furthermore, surfactants are described as amphiphilic substances which are able to dissolve organic, nonpolar substances in water. As a result of their specific molecular structure with at least one hydrophilic and one hydrophobic molecular moiety, they bring about a reduction in the surface tension of water, the wetting of the skin, the ease of soil removal and dissolution, ease of rinsing off and as desired— foam regulation. These substances are therefore also used as foam formers.

The hydrophilic fractions of a surfactant molecule are mostly polar functional groups, for example $-COO^-$, $-OSO_3^{2-}$, $-SO_3^-$, whereas the hydrophobic moieties are generally nonpolar hydrocarbon radicals. Surfactants are generally classified according to type and charge of the hydrophilic molecular moiety. In this connection, four groups can be differentiated:
anionic surfactants,
cationic surfactants,
amphoteric surfactants and
nonionic surfactants.

Anionic surfactants generally have carboxylate, sulfate or sulfonate groups as functional groups. In aqueous solution, they form negatively charged organic ions in an acidic or neutral medium. Cationic surfactants are almost exclusively characterized by the presence of a quaternary ammonium group. In aqueous solution, they form positively charged organic ions in an acidic or neutral medium. Amphoteric surfactants contain both anionic and cationic groups and behave accordingly in aqueous solution as anionic or cationic surfactants depending on the pH. In a strongly acidic medium, they have a positive charge and in an alkali medium a negative charge.

Surprisingly, it has been found that a thick-liquid, high viscosity lipid-containing preparation can be converted to a low viscosity and therefore sprayable state through the mere dissolving in the propellant gas, advantageously in n-butane, in the weight ratio according to the invention. Furthermore, in accordance with the invention, additives such as surfactants or solvents such as short-chain alcohols are dispensed with.

These additives cause disadvantages, as explained, which are to be avoided.

After the spraying, the preparation according to the invention can be readily distributed. In this connection, it has surprisingly been found that some of the propellant gas which is dissolved in the preparation does not escape directly after spraying, but only at a later time, within minutes.

In the moment after spraying, the formulation is accordingly still present as a mixture with parts of the propellant gas. The structure that is formed as a result and the gradual escape of the propellant gas produce a pleasantly tingling skin feel, which is perceived sensorily as positive. As a result of the subsequent escape and the cold due to evaporation associated therewith, a longer lasting cooling effect may additionally arise which constitutes a further bonus effect of the formulation according to the invention compared to prior art preparations.

An escaping of the propellant gas can be accelerated by rubbing the mixture. It is thus possible to individually influence the skincare and the sensory impression.

Following evaporation of the propellant gas, a skincare film as in the event of manual application from the tube is present, although, surprisingly, this is perceived as less unpleasant. It is particularly advantageous that a particularly thin product film can be generated on the skin by means of the spraying.

Compared to application from the tube and rubbing by hand, as a result of the application according to the invention, about 30% of preparation may be saved, and the same or a more pleasant care feel is nevertheless conveyed.

This is an advantage both for the user, who receives a less greasy feel, as well as for material use since less product for achieving the same effect is necessary.

Compared to U.S. Pat. No. 8,795,635 B2, according to the invention the addition of the so-called foam helpers, in particular surfactants, is dispensed with.

It is not the primary aim to produce a foam according to the invention. Rather, a new product performance is created which could be described less as foam but more as mousse.

Furthermore, in contrast to the prior art, the weight fraction of the lipid-containing preparation according to the invention compared to the propellant gas is less than 70% by weight, in particular in the range from 60:40% by weight to 40:60% by weight, ideally in the range around 50:50% by weight, based on the total mass of preparation and propellant gas.

In this connection, for example in US 20120189557 A1, preparations with a propellant gas fraction of 42.86% by weight are described as being nonusable, which is now possible in accordance with the invention.

The propellant-gas-containing formulations described in US 20120189557 A1 which, as a further difference, obligatorily comprise readily volatile solvents, such as silicones, therefore comprise propellant gases up to a fraction of 32.94% by weight.

Fractions in the region around 50% by weight particularly preferred according to the invention are described as nonusable.

WO 2014043487 A2 describes antiperspirant preparations in which the propellant gas fraction can be in the range from 30 to 65% by weight. This is achieved in the prior art only by a high fraction of nonvolatile silicones such as dimethicone (50 centistokes).

According to the invention, the propellant gases chosen are only substances from hydrofluorocarbons, n-butane, isobutane and propane or mixtures thereof. Very particularly preferred propellant gases are n-butane, isobutane and propane (either alone or as mixtures of two or three thereof), in particular n-butane.

Known alternatives to the HCFCs-based propellant gases for aerosol atomization are for example so-called HFAs, hydrofluoroalkanes, which do not adversely affect the ozone layer, but do promote the greenhouse effect. A further disadvantage of HFAs is that they cannot be used for all active-ingredient-containing preparations.

In the test, it was moreover found that high viscosity preparations could not be applied as well by means of HFAs. When using other propellant gases, such as dimethyl ether (DME), no or poor solubility of the preparation according to the invention results and sprayability can therefore not be achieved.

HFAs are therefore less preferred propellant gases than hydrocarbons.

It has proved to be advantageous for the propellant gas to be n-butane in combination with isobutane and/or propane, where the weight ratio of n-butane to the other propellant gases can be advantageously selected in the range from 100% by weight:0% by weight, from 99.9% by weight:0.1% by weight to 90% by weight:10% by weight, based on the total weight of the propellant gases.

In particular, a propellant gas mixture of 95% n-butane and 5% propane, in particular pure n-butane, thus 100% n-butane and 0% other propellant gases, has proved to be advantageous.

Propane is preferably selected as another lipophilic propellant (i.e., in addition to n-butane).

According to the invention, besides the propellant gases listed above, the formulation comprises no further propellant gases and no solvents which have a boiling point in the range from 30 to 150° C.

In particular, the preparation according to the invention comprises no petroleum spirit, and no monohydric alcohols with 2 to 6 carbon atoms, such as ethanol, propanol, isopropanol.

Volatile solvents, as described below, are likewise preferably dispensed with.

Organic solvents are volatile compounds which dissolve or dilute other substances (e.g. dyes) without changing them chemically.

They are mostly substance mixtures and not individual substances. The mixtures are generally composed of the substance classes of the aldehydes, ketones, aliphatic and aromatic hydrocarbons, alcohols and esters.

The aromatic hydrocarbons include e.g. benzene, toluene, ethylbenzene, xylene, styrene.

The aliphatic hydrocarbons include e.g. hexane, pentane, octane, decane, dodecane. They are often used solvents.

Terpenes (e.g. alpha-pinene, delta-3-carene and limonene) are often referred to as "natural" solvents, but are nevertheless not harmless in certain circumstances. They originate from pine and spruce wood and are increasingly used in paints and adhesives. Limonene occurs inter alia in the peels of citrus fruits and is added as citrus scent substitute to many kitchen products (detergents and dishwashing detergents etc.).

Chlorinated hydrocarbons (e.g. trichloroethene, 1,1,1-trichloroethane, tetrachloroethylene, perchloroethylene [PER]) should in principle be dispensed with in cosmetics.

Aldehydes, ketones and esters, such as e.g. ethanol, ethyl acetate, butyl acetate, hexanal, acetone, are known solvents and serve inter alia as diluents, shine improvers and cleaning agents.

Further solvents, which are preferably dispensed with in accordance with the invention, are 2-butanone, acrolein, chloroform, cyclohexane, cyclohexanone, dichloromethane, ethylbenzene, ethylene oxide, heptane, isoaliphatics, methylcyclohexane, trimeric 2-methylpropene and petroleum spirit.

Petroleum spirit is a mixture of hydrocarbons that are liquid at room temperature (20°-25° C.).

According to the invention, the fraction of silicones is also preferably selected to be a fraction of less than 40% by weight, in particular less than 20% by weight or less than 10% by weight and particularly preferably less than 5% by weight, based on the total mass of the preparation without propellant gases.

The silicones disclosed in US 20120189557 and WO 2014043487 A2 are advantageously dispensed with. These are in particular nonvolatile silicones, polyalkylsiloxanes, polyalkylarylsiloxanes and polyether siloxane copolymers.

In the lipid-containing preparation, preferred lipids may be one or more lipids selected from natural waxes, synthetic waxes, fatty acids and esters of fatty acids, as well as liquid, semisolid and solid hydrocarbons.

The lipid-containing preparation preferably contains at least 80% by weight, e.g., at least 85% by weight, at least 87% by weight, at least 89% by weight, at least 92% by weight, at least 95% by weight, at least 97% by weight, at least 98% by weight, at least 99% by weight, or at least 99.5% by weight of the one or more lipids, based on the total mass of the preparation.

The term lipid/wax is usually understood as meaning all natural or synthetically obtained substances and substance mixtures.

According to the invention, lipids that may be used include also fats and fat-like substances with a wax-like consistency. These include, inter alia, fats (triglycerides), mono- and diglycerides, natural and synthetic waxes, fatty alcohols and wax alcohols, esters of fatty alcohols and fatty acids, and fatty acid amides or any desired mixtures of this substance.

The waxes are particularly preferably selected from fats, in particular from natural waxes:

Shorea Stenoptera Seed Butter, Hydrogenated Vegetable Oil, Hydrogenated Coco-Glycerides, butyrospermum Parkii Butter, Theobroma Cacao (Cocoa) Seed Butter, Mango Butter, Hydrogenated Palm Kernel Glycerides, Hydrogenated Palm Glycerides, Sunflower Seed Wax, Soybean Glycerides, butyrospermum Parkii Unsaponifiables, wool wax, Cera Alba, beeswax, sugarcane wax, Cera Carnauba, Candelilla wax, Japan wax, Hydrogenated Rapeseed Oil, Shellac Wax, Hydrogenated Lecithin, Hydrogenated Soybean Oil, from synthetic waxes, in particular from:

Cera Microcristallina, Synthetic Beeswax, Synthetic Wax, Polyethylene, Paraffin Wax, ceresin, Ozokerite from fatty acids, in particular from:

Palmitic Acid, Stearic Acid, from esters of fatty acids, in particular from:

Cetearyl Nonanoate, Methyl Palmitate, Glyceryl Tribehenate, Glyceryl Laurate, Glyceryl Stearate, Cetyl Palmitate; Shea Butter oleyl esters, PEG-8 Beeswax.

Advantageous lipids exhibit a $T_{onset}$< of 30° C. These include, inter alia, fats (triglycerides), mono- and diglycerides, natural and synthetic waxes, fatty alcohols and wax alcohols, esters of fatty alcohols and fatty acids, and fatty acid amides or any desired mixturs of this substance.

Particularly preferably, the waxes are selected from fats, in particular from:

Shorea Stenoptera Seed Butter ($T_{onset}$=14.9° C.)
Hydrogenated Vegetable Oil ($T_{onset}$=18.9° C.)
Hydrogenated Coco-Glycerides ($T_{onset}$ 2=26.8° C.)
butyrospermum Parkii Butter ($T_{onset}$=28.3° C.)
Theobroma Cacao (Cocoa) Seed Butter ($T_{onset}$=14.5° C.)
Mango Butter ($T_{onset}$=19.4° C.)
Hydrogenated Palm Kernel Glycerides and Hydrogenated Palm Glycerides (Lipocire A, Gattefosse) ($T_{onset}$=20.3° C.)
Acacia Decurrens/Jojoba/Sunflower Seed Wax Polyglyceryl-3 esters ($T_{onset}$=14.4° C.) from esters from fatty acids, in particular from
Cetearyl Nonanoate ($T_{onset}$=24° C.)
Methyl Palmitate ($T_{onset}$=27.7° C.), and from fatty alcohols, in particular from
Cetearyl Alcohol ($T_{onset}$=28.1° C.).

The waxes preferred according to the invention melt above 20° C. without decomposition. They are low-viscosity and non-thread-drawing just a little above the melting point and exhibit considerable temperature-dependent consistency and solubility. According to the invention, it is possible to use a wax component or a mixture of wax components which starts to melt at a temperature $T_{onset}$<30° C. but is/are still solid at RT (20° C.). I.e. at least one wax has a melting point $T_{onset}$<30° C. or advantageously all selected waxes have this melting point.

$T_{onset}$ is determined by means of DSC.

DSC (Differential Scanning calorimetry) is a thermal method for measuring released/absorbed amount of heat of a sample during an isothermal procedure, heating or cooling (see DIN 53765, DIN 51007, ASTM E 474, ASTM D 3418). DSC is a comparative measurement method which permits the determination of amounts of heat of physical and chemical processes. If a material changes its physical state, such as e.g. melting or converting a crystal form to another or if it reacts chemically, heat is absorbed or released. These amounts of heat can be measured quantitatively with the help of DSC. The method runs cyclically, meaning that after the first heating curve a defined cooling takes place and then the sample is heated again within the stated temperature range. Two kinds of information are thus obtained: in the first heating curve, all thermal effects including prior history are evident. In the second heating curve, the prior history has been eliminated and the pure thermal behavior of the sample can be evaluated under defined cooling conditions. The melting temperature $T_{onset}$ of the waxes is ascertained during the second heating curve. By contrast, the melting range of the hydrodispersion between 5° C. and 30° C. according to DSC is the range ascertained in the first heating curve.

Further lipids and/or oils are preferably selected from polar oils, for example from lecithins and fatty acid triglycerides, namely the triglycerol esters of saturated and/or unsaturated, branched and/or unbranched alkanecarboxylic acids of chain length from 8 to 24, in particular 12 to 18 carbon atoms. The fatty acid triglycerides can advantageously be selected, for example, from synthetic, semisynthetic and natural oils, such as e.g. cocoglyceride, olive oil, sunflower oil, soyabean oil, peanut oil, rapeseed oil, argan oil, almond oil, palm oil, coconut oil, castor oil, wheatgerm oil, grapeseed oil, safflower oil, evening primrose oil, macadamia nut oil, to name just a few.

Further advantageous polar oil components can also be selected, within the context of the present invention, from the esters of saturated and/or unsaturated, branched and/or unbranched alkanecarboxylic acids of chain length from 3 to 30 carbon atoms and saturated and/or unsaturated, branched and/or unbranched alcohols of chain length from 3 to 30 carbon atoms, and also from the esters of aromatic carboxylic acids and saturated and/or unsaturated, branched and/or unbranched alcohols of chain length from 3 to 30 carbon atoms. Such ester oils can then advantageously be selected from octyl palmitate, octyl cocoate, octyl isostearate, octyldodeceyl myristate, octyldodecanol, cetearyl isononanoate, isopropyl myristate, isopropyl palmitate, isopropyl stearate, isopropyl oleate, n-butyl stearate, n-hexyl laurate, n-decyl oleate, isooctyl stearate, isononyl stearate, isononyl isononanoate, 2-ethylhexyl palmitate, 2-ethylhexyl laurate, 2-hexyldecyl stearate, 2-octyldodecyl palmitate, stearyl heptanoate, oleyl oleate, oleyl erucate, erucyl oleate, erucyl erucate, tridecyl stearate, tridecyl trimellitate, and synthetic, semisynthetic and natural mixtures of such esters, such as e.g. jojoba oil.

In addition, the lipid phase may advantageously be selected from dialkyl ethers and dialkyl carbonates. Advantageous are e.g. dicaprylyl ether (Cetiol OE) and/or dicaprylyl carbonate, for example that available under the tradename Cetiol CC from Cognis.

Furthermore, the lipid phase may likewise advantageously also comprise nonpolar oils, for example those which are selected from branched and unbranched hydrocarbons, in particular mineral oil, Vaseline (petrolatum), paraffin oil, squalene and squalene, polyolefins, hydrogenated polyisobutenes and isohexadecane. Among the polyolefins, polydecenes are the preferred substances.

Preference is given to selecting natural oil, vegetable oil or mineral oil, in particular paraffinum liquidum, in particular in a fraction of in each case 2% to 4% by weight, based on the total mass of the preparation.

The preparations according to the invention can optionally have a content of cyclic and/or linear silicone oils, where their fraction is obligatorily selected below 40% by weight, based on the total mass of the propellant-gas-free preparation.

Preferably, the preparation according to the invention comprises no silicones of any kind.

Preferred lipids are selected from mineral oil, in particular paraffinum liquidum, ceresin, lanolin alcohol and Cera Microcristallina.

A particularly preferred lipid is Cera Microcristallina.

Cera Microcristallina is the generic term for the alternative name such as microcrystalline wax, and Cire Minerale. Cera Microcristallina is a complex combination of long, branched hydrocarbon chains which are obtained from residual oils by solvent crystallization. Cera Microcristallina consists primarily of saturated straight and branched hydrocarbon chains, predominantly with more than 35 carbon atoms. Cera Microcristallina can be understood as meaning a mixture of a medical white oil and a paraffin wax. Cera Microcristallina was previously termed Vaseline®, which is nowadays supplied as a brand name by Chese Borough Ponds.

Vaseline (also Vaselin, pharmaceutical Vaselinum album="white Vaseline", Vaselinum flavum="yellow Vaseline") is an ointment-like mixture of solid and liquid hydrocarbons from petroleum with a melting range from 38 to 58° C.

In the same way, petrolatum is also discussed instead of Cera Microcristallina. Petrolatum is an ointment-like hydrocarbon mixture, also known as Vaseline, petroleum jelly or paraffin. Cera Microcristallina is subject to high quality standards. The Cera Microcristallina used according to the invention is free from, for example, polycyclic aromatics, sulfur-containing compounds and allergens. The observance of the quality criteria is regularly checked by independent authorities and in-house quality assurance.

Moreover, Cera Microcristallina comprises no residues from crop protection compositions and, on account of its chemical neutrality, has no allergenic potential.

Allergic reactions triggered by Cera Microcristallina are not known to date.

Compared to animal or plant oils, Cera Microcristallina has a high oxidation stability, i.e. it does not turn rancid and requires no additional stabilizers. Cera Microcristallina and thus also the preparations comprising it therefore also need no or few amounts of additional preservatives.

The skincare properties of Cera Microcristallina are primarily in the area of skin wetting. Cera Microcristallina forms a partially occlusive protective film on the skin which protects the skin from drying out. This is very important particularly for dry skin or highly stressed skin with a disturbed skin barrier. Partially occlusive care products position themselves in the upper horny layer and thus reduce the transepidermal water loss. In combination with other skin moisturizers (e.g. glycerin), they help to rapidly restore the equilibrium in the skin.

It is also to be noted that very similar substance mixtures, the so-called mineral waxes, are present naturally in relatively large amounts also in various plant waxes (e.g. Candellila wax) and insect waxes (e.g. beeswax).

The grade of the medical white oil is important for the production of Cera Microcristallina.

These compounds are substance mixtures which have a different composition depending on origin. For example, products which have been obtained from geologically old Venezuelan petroleum are particularly rich in naphthenes (cycloalkanes). The geologically young North Sea oil, by contrast, is low in napthenes and comprises predominantly acyclic compounds. Naphthene-rich mineral oils are present only in selected areas of the world (Venezuela, Saudi Arabia, Russia). They are difficult to isolate and accordingly expensive. Low-naphthene mineral oils are easier to obtain and are to be regarded as more cost-effective. A disadvantage of the low-naphthene mineral oils is that these oils or mixtures with these oils (inter alia Cera Mikrokristallina) used in emulsions destabilize the emulsions, which results in a considerable oil deposition.

Naphthenes or alicyclic hydrocarbons are ring-shaped hydrocarbons. The naphthene content of crude oil is generally 5%, in the case of Russian oil it is often more than this, and in the case of American oil less than this. Naphthenes have a higher bond tension than paraffins in the molecular structure and therefore have a higher heating value.

Cycloalkanes (cycloparaffins) are saturated ring-shaped hydrocarbons of the general formula CnH2n (n=3, 4, 5 . . . ), the names of which are formed from that of the corresponding alkane and the prefix cyclo–. The cycloalkanes, inter alia cyclopentane and cyclohexane, occurring in petroleum are also called naphthenes.

Preferably, therefore, naphthene-containing medical white oils should be used for producing Cera Microcristallina.

The formulations according to the invention are anhydrous. However, if water is present in the preparations on account of raw material impurities or other entrainments, then these preparations still qualify according to the invention as being "free from water", provided the water fraction is not above 2% by weight, e.g., not above 1% by weight, or not above 0.1% by weight, in particular not above 0.02% by weight, based on the total mass of the preparation.

The formulation according to the invention will usually be present in a pressurized gas container, an aerosol, preferably in a transparent container, in which the preparation is in contact with the propellant gas.

The pressure stages are preferably selected in the range from 1 to 4 bar. Known propellant gas mixtures, such as propane, butane, isobutane, have pressure stages of 2.7 bar.

The current standard in the cosmetics industry is a pressurized gas container made of metal, preferably aluminum.

Transparent container means that its wall has a transmittance for visible light of 25% to 100%.

Also therefore in accordance with the invention is the use of a formulation comprising
    an anhydrous, lipid-containing cosmetic preparation with a weight fraction of ethanol, methanol, isopropanol, petroleum spirit and surfactants of in each case less than 0.1% by weight and a weight fraction of silicone compounds of less than 40% by weight, based on the total mass of the preparation, and propellant gas consisting essentially of one or more substances selected from hydrofluorocarbons, n-butane, isobutane and propane, where the lipid-containing preparation is in direct contact with the propellant gas and the weight fraction of the lipid-containing preparation is less than 70% by weight, based on the total mass of the formulation, for the application of the preparation from a pressurized gas container on to the skin.

The preparation can be discharged from the container via a discharge device. Suitable discharge devices are known in the prior art.

By triggering the corresponding spray head, the mixture of propellant gas and lipid preparation escapes for example through a rising tube and/or via a valve. The gas can then expand again. Then, normally, on account of the ambient pressure small gas bubbles of the propellant gas are formed in the lipid preparation, as a result of which a foam can be generated, particularly if foam formers are present. Foams here do not require a high propellant gas fraction since relatively high propellant gas fractions would lead to a breakdown of the fill material into smaller and finer droplets and the contents would then discharge in a very fine mist.

Also in the event of the high consistency of the lipid-containing preparation, however, no immediate gas bubble formation is observed but, as described previously, a sensorily pleasant product application.

The filling of pressurized gas containers, such as aerorol cans, is based on the following principle and is prior art:

filing of the empty and open aerosol can with liquid preparation crimping of the can with a valve gassing of the aerosol can through the valve with the liquid propellant gas.

A propellant gas fraction of 35 to 65% by weight, in particular 40 to 60% by weight, particularly preferably around 50% by weight, based on the total mass of the formulation, has been ascertained as a ratio that is particularly advantageous according to the invention.

Comparative experiments with different propellant gas mixtures reveal that a particularly advantageous application and product performance is ensured especially for weight ratios of n-butane to propane of 90:10 to 100:0.

For propellant gas mixtures as in the prior art and also ratios of preparation to propellant gas that are not in accordance with the invention, by contrast, streaks remain on the vessel wall and the product can not be emptied completely at all or very easily.

The formulation according to the invention can advantageously comprise further substances provided the features according to the invention are still taken into consideration.

In a particularly preferred embodiment, the preparations in the context of the present invention comprise so-called moisturizers. Moisturizers is the term used to refer to substances or substance mixtures which impart to cosmetic preparations the property, following application and/or spreading on the skin surface, of reducing the moisture release from the horny layer (also termed transepidermal water loss (TEWL)) and/or of positively influencing hydration of the horny layer.

Advantageous moisturizers in the context of the present invention are, for example, glycerin, lactic acid and/or lactates. Further preferred skin moisturizers are in particular sodium lactate, butylene glycol, propylene glycol, biosaccaride gum-1, glycine soja, ethylhexyloxyglycerin, pyrrolidonecarboxylic acid, urea, glyceryl glucoside.

The amount of moisturizers, one or more compounds, is advantageously selected from the range from 1 to 20% by weight, preferably from 3 to 15% by weight, particularly preferably from 5 to 12% by weight, in each case based on the total weight of the preparation.

The cosmetic compositions in the context of the present invention can be used for example depending on their formulation, as skin protection cream, nutrient cream, day cream or night cream etc.

A surprising advantage of the preparation according to the invention is evident upon use. The formulation has a freshening and tingling effect on the skin as a result of the fact that the propellant gas which subsequently volatilizes brings about cooling due to evaporation. Associated therewith, the mixture of gas and preparation is firstly in the form of a cream-like preparation, the impression of which is characterized in that the gradually escaping propellant gas leaves behind a tingling skin feel.

A further advantage is achieved by the fact that upon discharging the formulations according to the invention a droplet size of much more than 10 nm is achieved.

The cosmetic or dermatological formulations according to the invention may also comprise cosmetic auxiliaries and active ingredients, as are customarily used in such formulations, e.g. preservatives, preservation aids, bactericides, substances for preventing foaming, dyes and colored pigments, thickeners, moisturizing and/or humectant substances, antiaging substances or other customary constituents of a cosmetic or dermatological formulation such as polyols, polymers, provided the addition does not adversely affect the required properties in respect of sensorics, care effects, or freedom from water and solvent.

A particularly preferred formulation consists of 50% by weight of n-butane as propellant gas and a lipid-containing preparation comprising Cera Microcristallina, mineral oil, ceresin and lanolin alcohols, and also glycerin and bisabolol as skincare active ingredients.

The particularly preferred formulation is free from water, foam formers, silicones and solvents with a boiling point above 30° C., and the weight fraction of the lipid-containing preparation relative to the propellant gas is in the range 45% by weight:55% by weight to 55% by weight:45% by weight, based on the total mass of the formulation consisting of lipid-containing preparation and propellant gas.

In another preferred embodiment thereof, the formulation is substantially free from film-forming agents such as, e.g., polyvinyl pyrrolidone, polyvinyl alcohol, (meth)acrylic polymers and copolymers, polyvinyl acetate, and cellulose-based polymers and copolymers.

Also in accordance with the invention is a method for applying a lipid-containing preparation with a high dynamic viscosity of more than 15 000 mPa*s and/or a consistency of 50 to 70 units, measured using the consistometer KO–82.

For this, the preparation is supplied with propellant gas in a suitable vessel with discharge device. The propellant gas consists of one or more substances, in particular hydrocarbons selected from the group n-butane, isobutane and propane, in particular only n-butane.

Upon discharging the preparation, a cream-like mousse is formed which feels pleasantly light in sensory terms and can be easily spread on the skin.

The "mousse" feels sensorily considerably lighter than the lipid-containing preparation without propellant gas discharge according to the invention, e.g. as upon application from a tube or a pot. The spreading of the formula on the skin is also considerably easier, and an overall thinner and more even product film can be produced. However, the mousse is also solid enough to attach to the skin and as a result be able to be spread in an agreeable manner and not lift off like a foam.

The formulation of the present invention may be prepared by, for example, by adding the previously prepared lipid-containing preparation and the liquid propellant gas or mixture of propellant gases to a suitable container, such as a spray can.

To sum up, the present invention provides in particular:

1. A topical formulation for application to skin, wherein the formulation comprises
   an anhydrous lipid-containing preparation with a weight fraction of ethanol, methanol, isopropanol, petroleum spirit and surfactants of in each case from 0% to less than 0.1% by weight and a weight fraction of silicone compounds of from 0% to less than 40% by weight, based on the total mass of the preparation, and
   propellant gas consisting essentially of one or more substances selected from hydrofluorocarbons, n-butane, isobutane and propane,
   the lipid-containing preparation being in direct contact with the propellant gas and the weight fraction of the lipid-containing preparation being less than 70% by weight, based on the total mass of the formulation.

2. A formulation according to item 1, wherein the lipid-containing preparation exhibits a dynamic viscosity of more than 10 000 mPa*s, preferably a dynamic viscosity in the range from 15 000 to 30 000 mPa*s, and particularly preferably in the range from 18 000 to 25 000 mPa*s, measured at 25° C. and with a shear rate of 10 s$^{-1}$.

3. A formulation according to any one of items 1 to 3, wherein the lipid-containing preparation has a consistency of 50 to 70 units, measured using a consistometer at 25° C.

4. A formulation according to any one of the preceding items, wherein the weight ratio of lipid-containing preparation to propellant gas is from 69% by weight:31% by weight to 10% by weight:90% by weight, in particular from 65% by weight:35% by weight to 10% by weight:90% by weight, in particular in the range from 60% by weight:40% by weight to 40% by weight:60% by weight, in particular in the range from 55% by weight:45% by weight to 45% by weight:55% by weight, very particularly preferably 50% by weight:50% by weight, based on the total mass of the formulation.

5. A formulation according to any one of the preceding items, wherein the propellant gas is n-butane, alone or in combination with isobutane and/or propane.

6. A formulation according to item 5, wherein the weight ratio of n-butane to the other propellant gases is in the range from 99.9% by weight:0.1% by weight to 90% by weight:10% by weight, based on the total weight of the propellant gases.

7. A formulation according to any one of the preceding items, wherein the propellant gas consists of n-butane.

8. A formulation according to any one of the preceding items, wherein the formulation is free from short-chain primary alcohols having 2 to 6 carbon atoms.

9. A formulation according to any one of the preceding items, wherein the formulation is free from solvents with a boiling point in the range from 30° C. to 150° C.

10. A formulation according to any one of the preceding items, wherein the formulation is free from foam formers.

11. A formulation according to any one of the preceding items, wherein the formulation is free from silicone compounds.

12. A formulation according to in any one of the preceding items, wherein the lipid-containing preparation comprises one or more lipids selected from Cera Microcristallina, Paraffinum liquidum, mineral oil, ceresin, lanolin alcohol.

13. A formulation according to any one of the preceding items, wherein the formulation comprises one or more of dexpanthenol, bisabolol, licochalcone A, polydocanol and zinc oxide.

14. A pressurized gas container which contains the formulation according to any one of items 1 to 13.

15. The use of propellant gas consisting essentially of one or more substances selected from hydrofluorocarbons, n-butane, isobutane and propane for applying an anhydrous, high-viscosity lipid-containing preparation from a pressurized gas container, wherein the preparation is in direct contact with the propellant gas and the weight fraction of the lipid-containing preparation is less than 70% by weight, based on the total mass of the preparation and propellant gas.

16. The use of a formulation comprising
   an anhydrous, lipid-containing cosmetic preparation with a concentration of ethanol, methanol, isopropanol, petroleum spirit and surfactants of in each case from 0% to less than 0.1% by weight and a weight fraction of silicone compounds of from 0% to less than 40% by weight, based on the total mass of the preparation, and
   propellant gas consisting essentially of one or more substances selected from hydrofluorocarbons, n-butane, isobutane and propane,
   where the lipid-containing preparation is in direct contact with the propellant gas and the concentration of the lipid-containing preparation is less than 70% by weight, based on the total mass of the formulation, for the application of the preparation from a pressurized gas container to the skin.

BRIEF DESCRIPTION OF THE DRAWINGS

In the accompanying drawings, FIGS. 1-10 are sketches of photographs which show test tubes containing mixtures of lipid-containing preparation and propellant gas in various weight ratios and with various propellant gas compositions.

DETAILED DESCRIPTION OF EMBODIMENTS OF THE INVENTION

The particulars shown herein are by way of example and for purposes of illustrative discussion of the embodiments of the present invention only and are presented in the cause of providing what is believed to be the most useful and readily understood description of the principles and conceptual aspects of the present invention. In this regard, no attempt is made to show details of the present invention in more detail than is necessary for the fundamental understanding of the present invention, the description in combination with the drawings making apparent to those of skill in the art how the several forms of the present invention may be embodied in practice.

The following experimental series reveal the advantages of the lipid-containing preparation with propellant gases at different mixing ratios, the results of which (photos or sketches of the photos) are shown in FIGS. 1 to 10.

Figure 1:
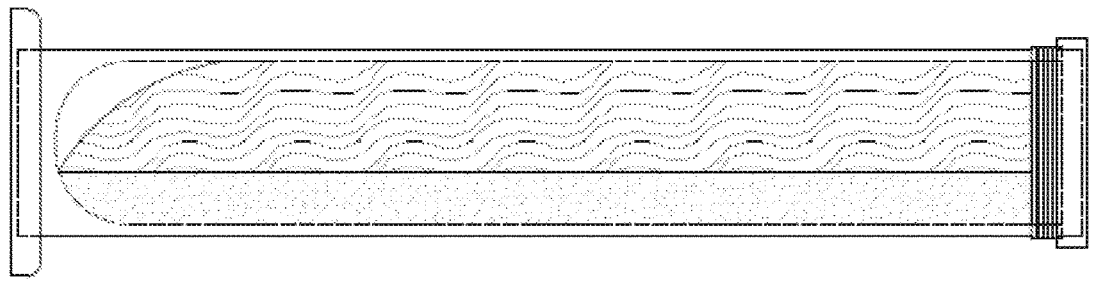
Figure 1:
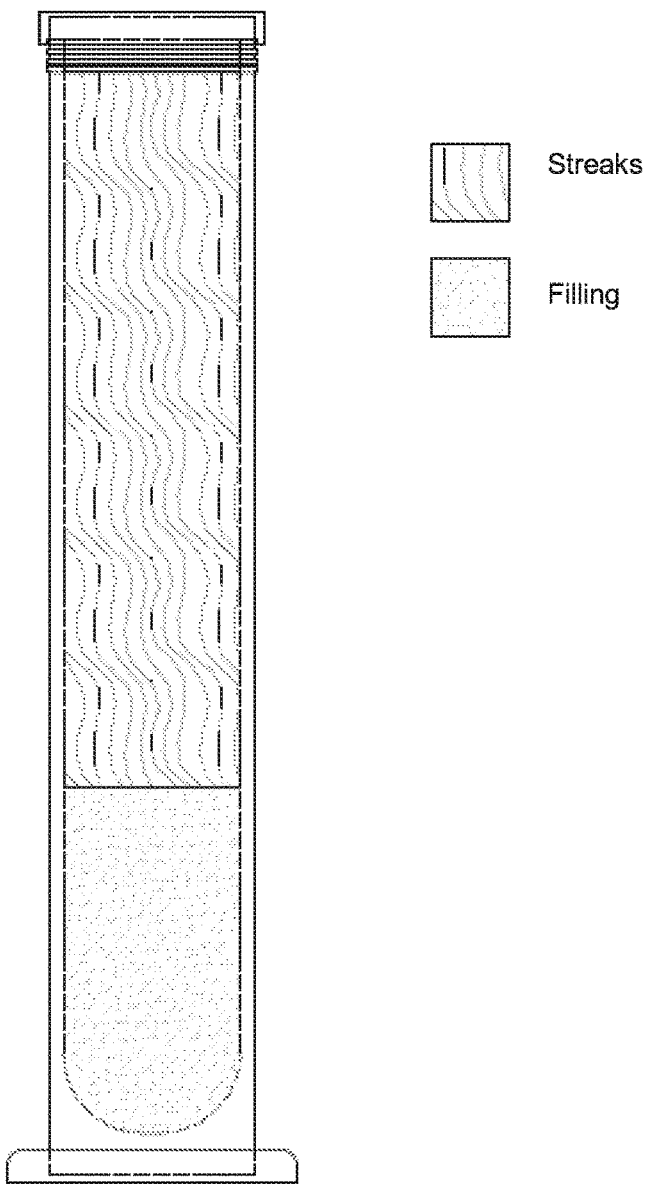
Figure 1:
Figure 1:

FIG. 1: 50% n-butane: 50% viscose lipid-containing preparation

The once (i.e. without propellant gas) high viscosity (24 860 mPa*s) lipid-containing preparation is present in the dissolved state at a mixing ratio of 50:50 (propellant gas: preparation). The sprayability of the formulation is ensured. This mixture is shown to be particularly preferred on account of the lowest streak formation.

Streak formation here is evidence of poor discharge.

Figure 2:
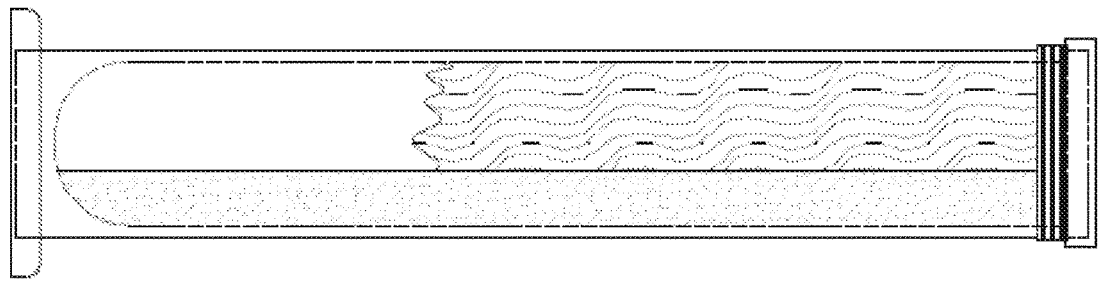
Figure 2:
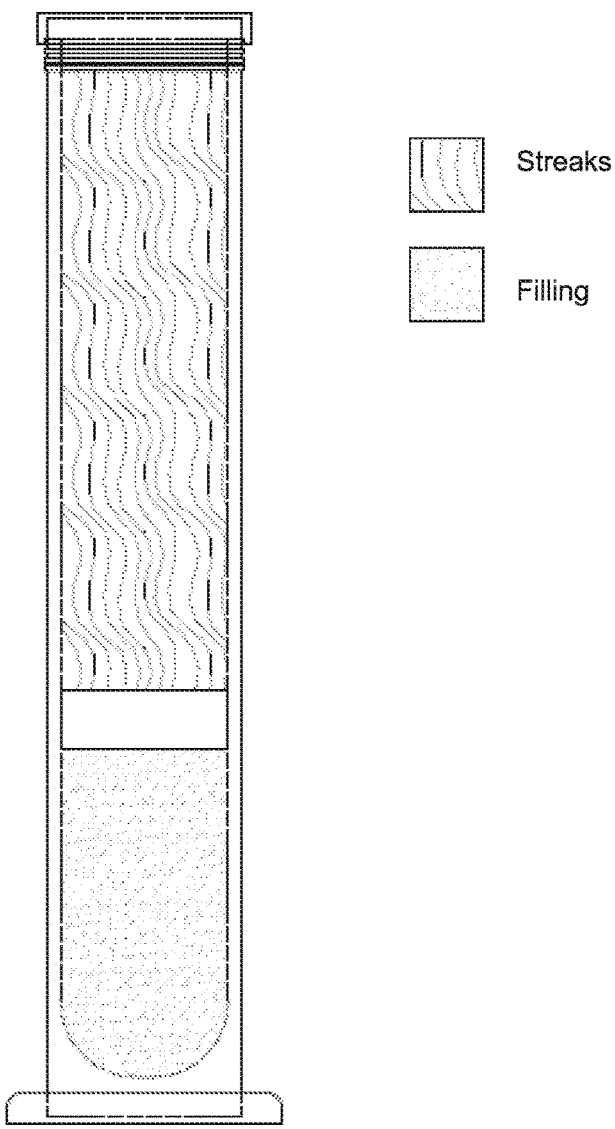
Figure 2:
Figure 2:

FIG. 2: 50% isobutane: 50% viscose lipid-containing preparation

The once high viscosity lipid-containing preparation is present in the dissolved state at a mixing ratio of 50:50. A thin film of formulation is observed on the container wall. The sprayability of the formulation is nevertheless ensured.

Figure 3:
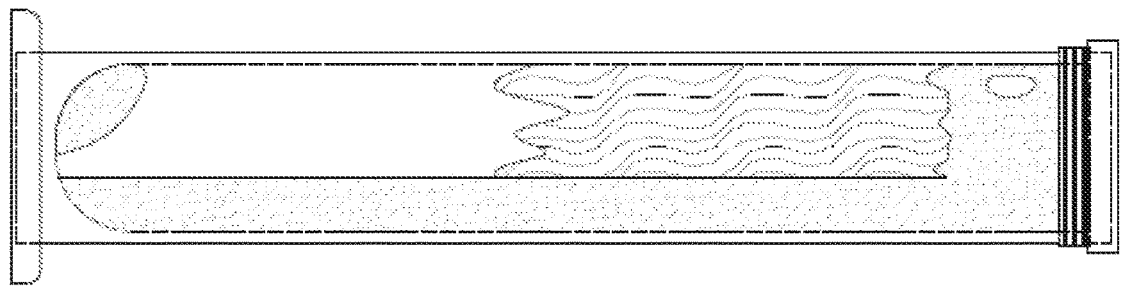
Figure 3:
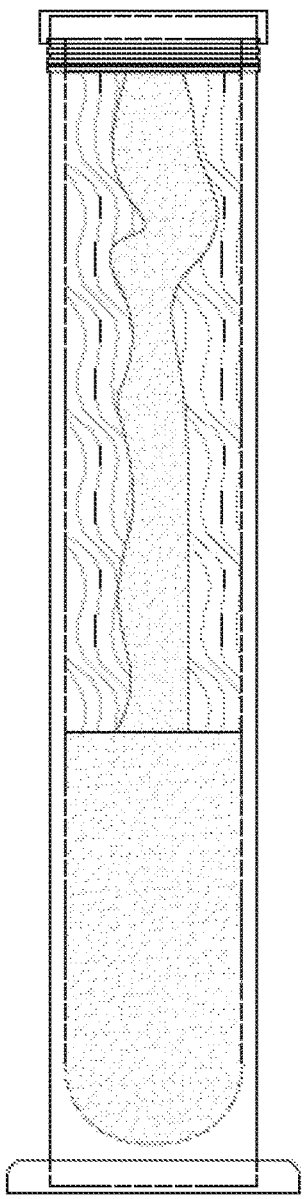
Figure 3:
Figure 3:

FIG. 3: 50% n-propane: 50% viscose lipid-containing preparation

The once high viscosity lipid-containing preparation is present in the dissolved state at a mixing ratio of 50:50. Deposits and a thin film of formulation are observed on the container wall. The sprayability of the formulation is ensured.

FIG. 4: 50% propellant gas mixture (consisting of 60% n-butane, 20% isobutane, 20% n-propane): 50% viscose lipid-containing preparation The once high viscosity lipid-containing preparation is present in the dissolved state at a mixing ratio of 50:50. Deposits and a thin film of preparation are observed on the container wall. The sprayability of the formulation is ensured.

Figure 5:
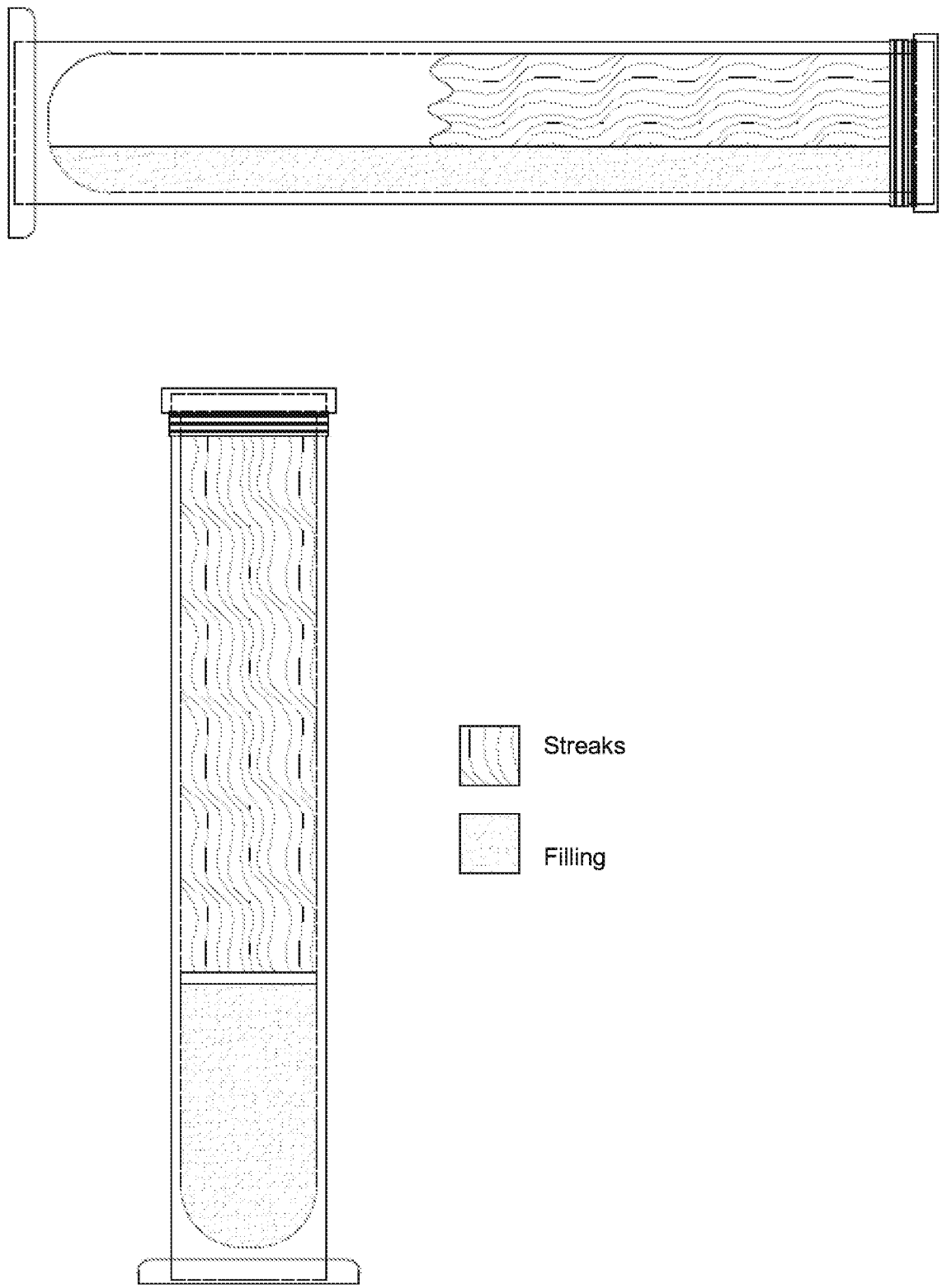

FIG. 5: 40% n-butane: 60% viscose lipid-containing preparation

The once high viscosity (18 410 mPa*s) lipid-containing preparation is present in a dissolved state at a mixing ratio of 40:60. Deposits and a thin film of formulation are observed on the container wall. The sprayability of the formulation is ensured.

FIG. 6: 40% isobutane: 60% viscose lipid-containing preparation

The once high viscosity lipid-containing preparation is present in the dissolved state at a mixing ratio of 40:60. Deposits and a thin film of formulation are observed on the container wall. The sprayability of the formulation is ensured.

Figure 7:
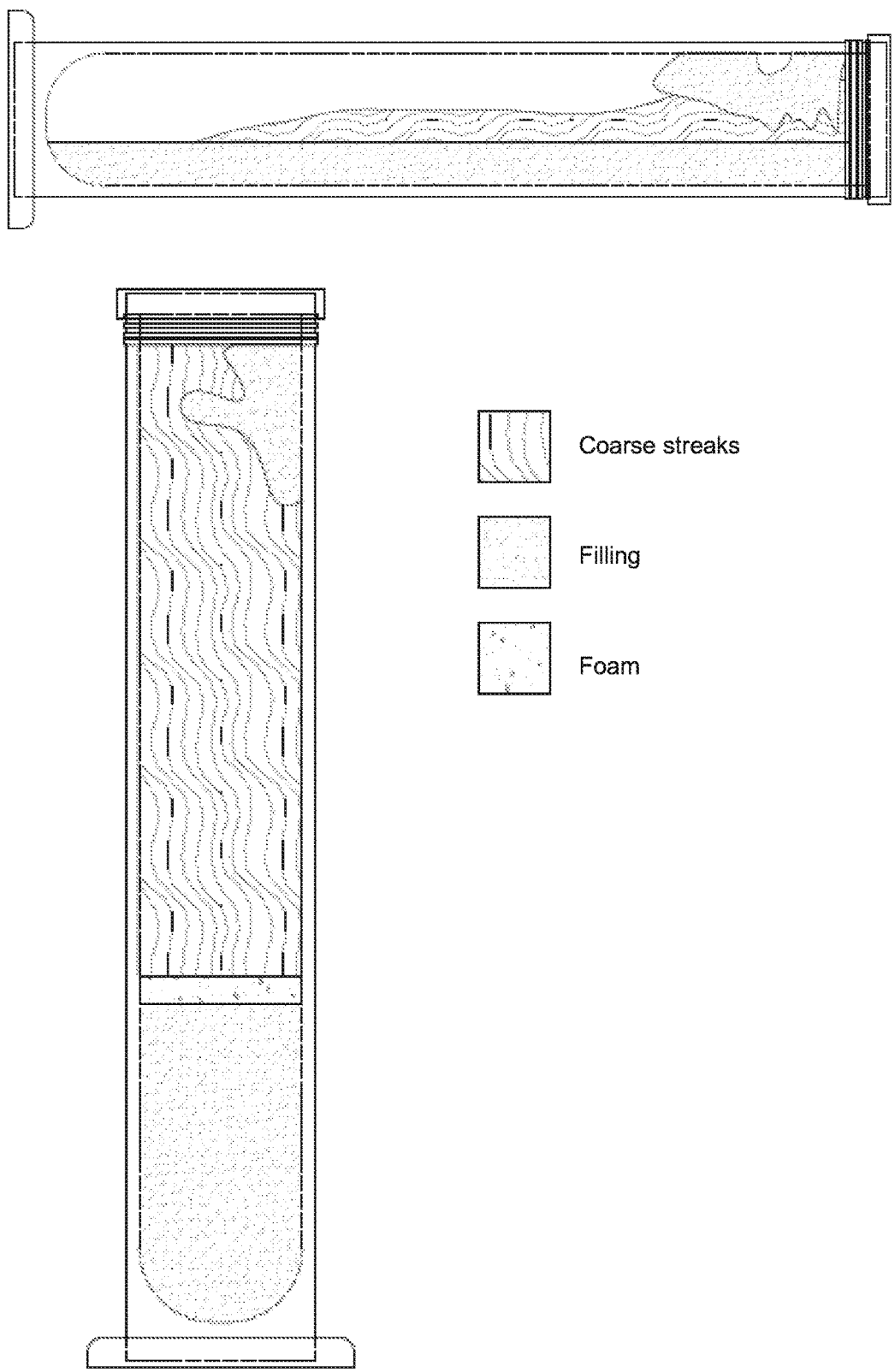

FIG. 7: 40% n-propane: 60% viscose lipid-containing preparation

The once high viscosity lipid-containing preparation is present in the dissolved state at a mixing ratio of 40:60. Deposits and a thin film of formulation are observed on the container wall. The sprayability of the formulation is ensured.

Figure 8:
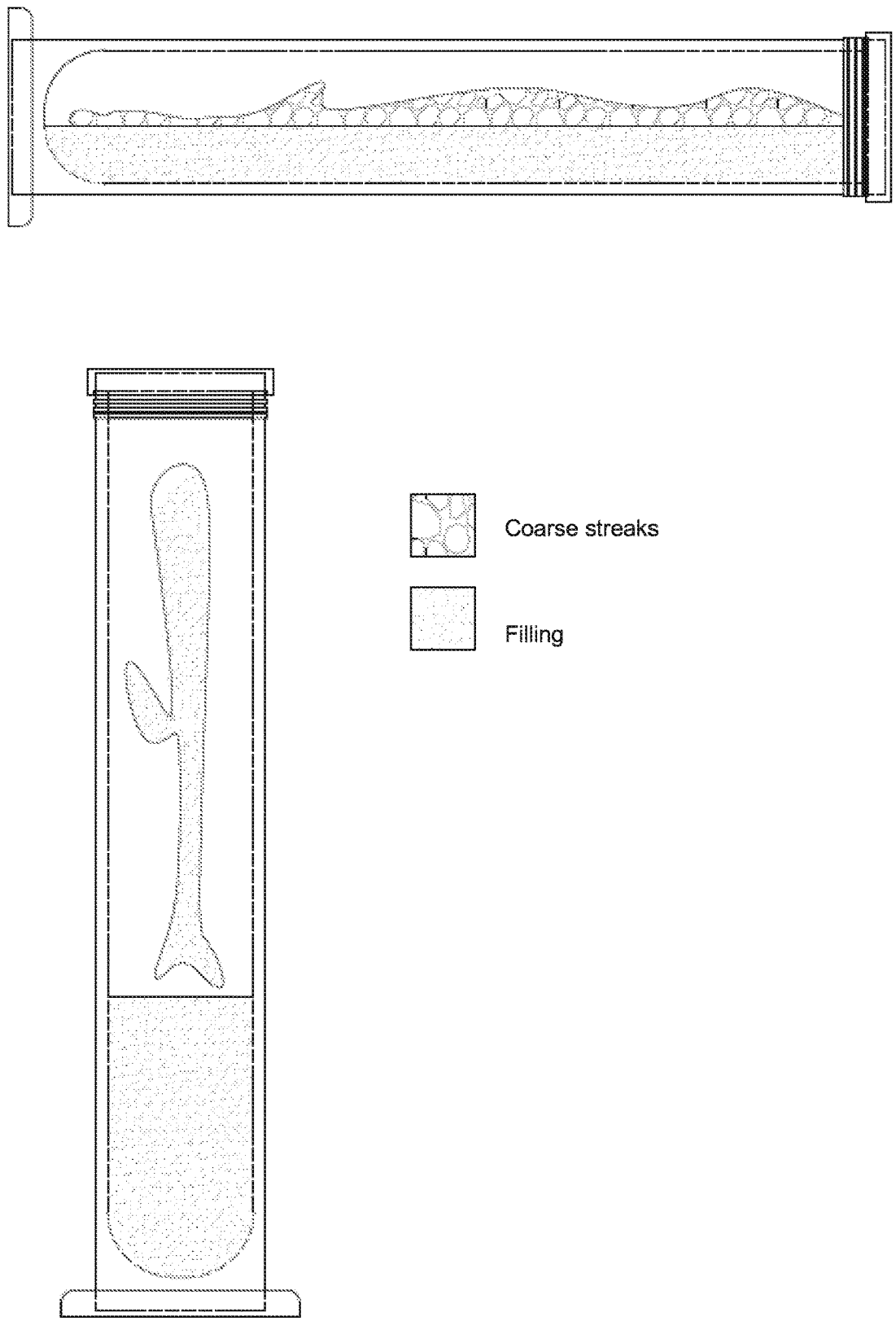

FIG. 8: 40% propellant gas mixture (consisting of 60% n-butane, 20% isobutane, 20% n-propane): 60% viscose lipid-containing preparation The once high viscosity lipid-containing preparation is present in the dissolved state at a mixing ratio of 40:60. Deposits and a thin film of formulation are observed on the container wall. The sprayability of the formulation is ensured.

FIG. 9: 30% n-butane: 70% viscose lipid-containing preparation

The once high viscosity (18 670 mPa*s) lipid-containing preparation is only partially in the dissolved state at a mixing ratio of 30:70. The sprayability of the formulation is not ensured.

Figure 10:
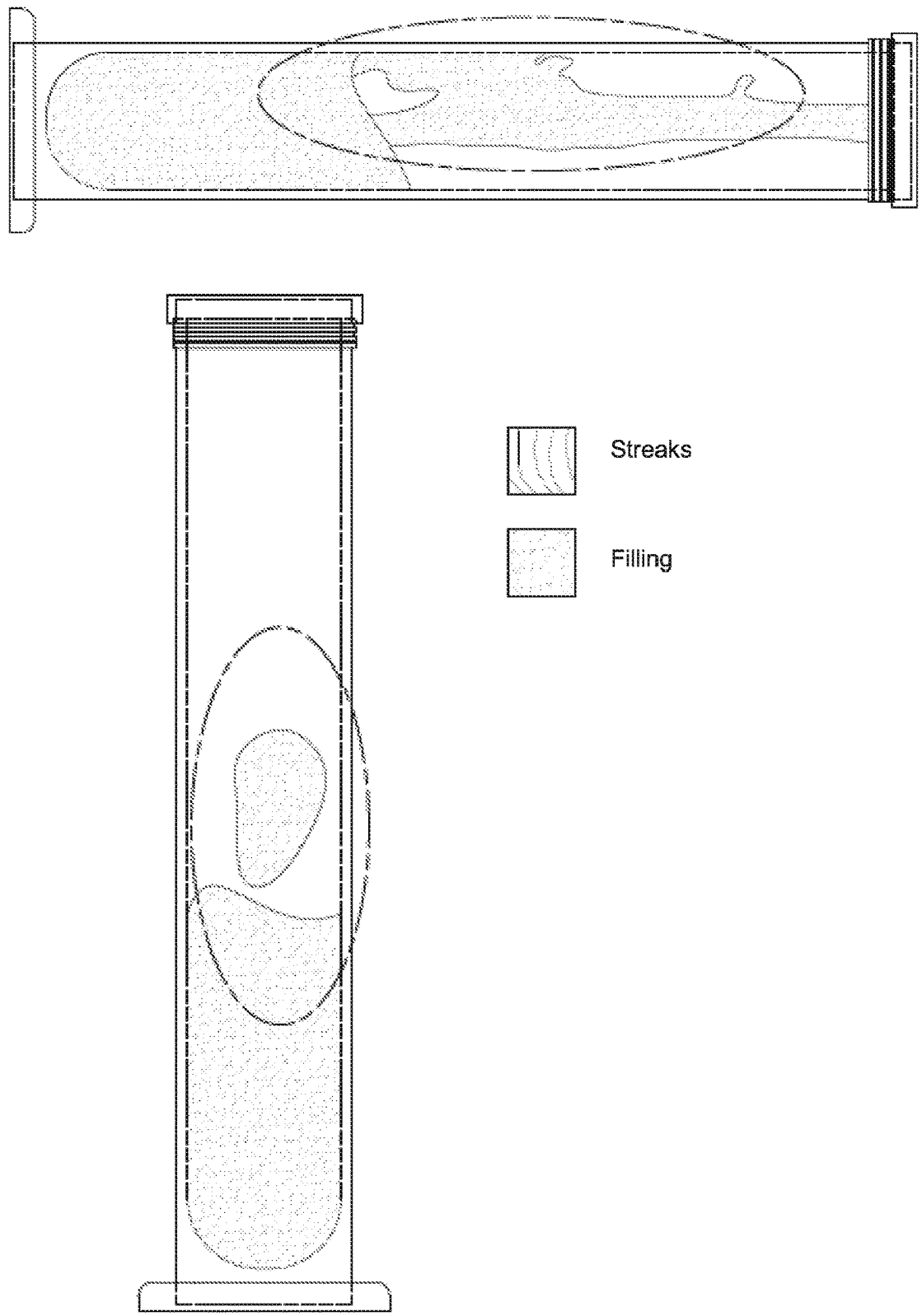

FIG. 10: 20% n-butane: 80% viscose lipid-containing preparation

The once high viscosity lipid-containing preparation is in a nondissolved state at a mixing ratio of 20:80. The sprayability of the formulation is not ensured.

The experiments reveal that a fraction of lipid-containing preparation of more than 70% by weight leads to a formulation that can no longer be applied.

The investigations also show that it is particularly preferred to select the ratio of propellant gas to lipid-containing preparation in the weight ratio from about 40:60 to 60:40, ideally 50:50.

In the case of a lower propellant gas fraction, there is no residue-free discharge and streaks remain on the vessel wall. The comparative experiments also show that a discharge of the preparation is unsuccessful and thus the advantages of freshening/cooling/tingling as well as good spreadability are not ensured.

Complete emptying, no streaks on the wall, no small drop formation and the formation of a cream capable of application is possible only with the specified propellant gases according to the invention (in particular butane, advantageously to 90% or 100%) and certain ratios of the lipid preparation to propellant gas, in particular in the region of about 50:50.

This result was surprising and could not be foreseen by the person skilled in the art.

The examples below illustrate the formulations according to the invention.

Unless stated otherwise, the numerical data refer to weight fractions based on the total mass of the preparation.

EXAMPLES

|  | 1 | 2 | 3 | 4 | 5 | 6 | 7 | 8 | 9 | 10 |
|---|---|---|---|---|---|---|---|---|---|---|
| Vaseline | 40 | 50 | 60 | 45 | 45 | 45 | 41.95 | 50 | 45 | 50 |
| Ceresin | 15 | 10 | 5.8 | 6 | 10 | 8 | 13 | 5 | 7 | 5 |
| Lanolin alcohol | 3 | 4 | 2 | 5 | 2 | 5 | 3 | 4 | 4 | 4 |
| Panthenol |  |  |  | 1.5 | 0.45 | 0.5 |  | 3 |  | 3 |
| Glycerin |  |  |  | 1.45 | 2 | 3 |  | 2 | 2 | 2 |
| Bisabolol |  |  |  | 0.5 |  | 0.5 |  |  |  | 0.5 |
| Liquid paraffin | 42 | 35 | 32 | 40.5 | 40.5 | 38 | 42 | 36 | 41.96 | 35.5 |
| Licochalocone A |  |  | 0.2 | 0.05 |  |  |  |  |  |  |
| Polyhexanide |  |  |  |  | 0.05 |  | 0.05 |  | 0.04 |  |
| Clotrimazole |  | 1 |  |  |  |  |  |  |  |  |

|  | 11 | 12 | 13 | 14 | 15 | 16 | 17 | 18 | 19 | 20 |
|---|---|---|---|---|---|---|---|---|---|---|
| Vaseline | 50 | 45 | 40 | 55 | 50 | 100 | 90 | 90 | 40 | 45 |
| Ceresin | 15 | 10 | 15 | 5 | 15 |  |  |  | 13 | 6 |
| Lanolin alcohol | 3 | 4 | 3 | 2 | 5 |  |  |  | 3 | 1.95 |
| Panthenol |  |  |  | 2 |  |  |  |  |  | 1.5 |
| Glycerin |  |  |  | 3 |  |  | 2 | 2 |  | 1.5 |
| Bisabolol |  |  |  | 0.5 |  |  |  |  |  | 0.5 |
| Liquid paraffin | 32 | 41 | 41.9 | 32.5 | 29.9 | 0 | 8 | 7.9 | 43.9 | 43.5 |
| Licochalocone A |  |  | 0.1 |  |  |  |  | 0.1 |  |  |
| Coenzyme Q10 |  |  |  |  |  |  |  |  |  | 0.05 |
| Octinidine dihydrochloride |  |  |  | 0.1 |  |  |  |  | 0.1 |  |

Compositions 1 to 20 were admixed with propellant gases n-butane or n-butane/propane in a weight ratio of 50:50.

|  | 21 | 22 |
|---|---|---|
| Bisabolol | 0.25 | 0.2 |
| Microcrystalline wax (Cera Microcristallina) | 41.0 | 27.1 |
| Ceresin | 15.0 | 15.0 |
| Farnesol | 0.25 | 0.0 |
| Glycerin | 1.0 | 1.0 |
| Lanolin alcohol | 3.0 | 3.0 |
| Panthenol | 1.0 | 1.0 |
| Paraffinum liquidum | 38.5 | 52.7 |
|  | 100% | 100% |
| Propellant gas |  |  |
| Propane | 50% | 50% |
| n-Butane | 50% | 50% |

All of the examples were found to be extraordinarily advantageous and pleasant both in sensory terms as well as in respect of ability to be applied.

It is noted that the foregoing examples have been provided merely for the purpose of explanation and are in no way to be construed as limiting of the present invention. While the present invention has been described with reference to exemplary embodiments, it is understood that the words which have been used herein are words of description and illustration, rather than words of limitation. Changes may be made, within the purview of the appended claims, as presently stated and as amended, without departing from the scope and spirit of the present invention in its aspects. Although the present invention has been described herein with reference to particular means, materials and embodiments, the present invention is not intended to be limited to the particulars disclosed herein; rather, the present invention extends to all functionally equivalent structures, methods and uses, such as are within the scope of the appended claims.

What is claimed is:

1. A topical formulation for application to skin, wherein the formulation comprises
    an anhydrous lipid-containing preparation, and
    propellant gas consisting essentially of one or more substances selected from hydrofluorocarbons, n-butane, isobutane and propane,
    the lipid-containing preparation being in direct contact with the propellant gas and comprising ethanol, methanol, isopropanol, petroleum spirit and surfactants in concentrations of in each case from 0% to less than 0.1% by weight and a concentration of silicone compounds of from 0% to less than 40% by weight, based on a total mass of the preparation, and
    a concentration of the lipid-containing preparation being not more than 61% by weight, based on a total mass of the formulation, and
    wherein the formulation is free from foam formers.

* * * * *